(12) United States Patent
Tamura et al.

(10) Patent No.: US 7,169,845 B2
(45) Date of Patent: Jan. 30, 2007

(54) POLYMERIZATION REGULATORS AND COMPOSITIONS FOR RESIN

(75) Inventors: Masaki Tamura, Kanagawa (JP); Takahiro Matsui, Osaka (JP); Masanori Shimuta, Mie (JP); Yuichi Yoshimura, Mie (JP); Motoharu Takeuchi, Tokyo (JP); Hiroshi Horikoshi, Tokyo (JP); Hiroyuki Okada, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 234 days.

(21) Appl. No.: 10/297,383

(22) PCT Filed: Apr. 4, 2002

(86) PCT No.: PCT/JP02/03388

§ 371 (c)(1),
(2), (4) Date: Dec. 6, 2002

(87) PCT Pub. No.: WO02/083763

PCT Pub. Date: Oct. 24, 2002

(65) Prior Publication Data

US 2003/0171533 A1    Sep. 11, 2003

(30) Foreign Application Priority Data

Apr. 6, 2001    (JP) .............................. 2001-109154
May 10, 2001    (JP) .............................. 2001-139614

(51) Int. Cl.
*C08L 81/00* (2006.01)
*C08K 3/16* (2006.01)

(52) U.S. Cl. ....................... 524/609; 524/742; 524/750; 524/751; 524/752; 524/792; 528/377; 528/378; 528/380

(58) Field of Classification Search ................. 524/609, 524/742, 750, 751, 752, 792; 528/377, 378, 528/380
See application file for complete search history.

(56) References Cited

U.S. PATENT DOCUMENTS

| | | | |
|---|---|---|---|
| 5,698,664 A | 12/1997 | Allcock et al. | |
| 6,486,298 B1 * | 11/2002 | Jallouli et al. | ............... 528/374 |
| 6,528,005 B2 * | 3/2003 | Amagai et al. | ........ 264/331.12 |
| 6,534,589 B1 * | 3/2003 | Yoshimura et al. | ......... 524/765 |

FOREIGN PATENT DOCUMENTS

| | | |
|---|---|---|
| GB | 1177766 | 1/1970 |
| GB | 1229041 | 4/1971 |
| GB | 1232622 | 5/1971 |
| WO | WO 01/70853 A2 | 9/2001 |
| WO | WO 02/055185 A2 | 7/2002 |

OTHER PUBLICATIONS

Abstract of an article published in Wuhan Daxue Xuebeon, Ziran Kexueban, 1990(1), 83-86.*
International Search Report, dated Jul. 16, 2002, for PCT/JP02/03388.
English Abstract of JP 2001-2784A, Jan. 9, 2001.
English Abstract of JP 2000-256463A, Sep. 19, 2000.
English Abstract of JP 2001-163978A, Jun. 19, 2001.
Supplementary European Search Report, for Application No. EP 02 71 3295, Dated Feb. 22, 2006.

* cited by examiner

*Primary Examiner*—Marc S. Zimmer
(74) *Attorney, Agent, or Firm*—Antonelli, Terry, Stout and Kraus, LLP.

(57) ABSTRACT

In the present invention, an episulfide compound having, in one molecule, at least one epithio structure represented by the following Formula 2:

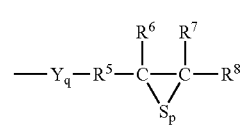

(2)

wherein $R^5$ is C1–C10 hydrocarbylene or single bond, $R^6$, $R^7$ and $R^8$ are each independently C1–C10 hydrocarbyl or hydrogen, Y is O, S, Se or Te, p is an integer from 1 to 5 and q is an integer from 0 to 5,
is polymerized in the presence of a halide of a 13–16 group element of the long periodic table and/or a polymerization regulator represented by the following Formula 1:

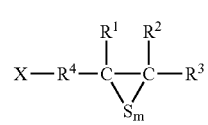

(1)

wherein $R^1$, $R^2$ and $R^3$ are each C1–C10 hydocarbyl or hydrogen, $R^4$ is C1–C10 hydrocarbylene or single bond, X is F, Cl, Br, I, As, SH, OH, C1–C10 alkoxyl, C1–C10 alkylthio, or C1–C10 mercaptoalkythio, and m is an integer from 1 to 5,
to produce a cured resin suitable as an optical material. By using the polymerization regulator, the polymerization rate of the episulfide compound can be suitably regulated to obtain a cured resin with less defect. By using the halide, the increase in the viscosity of the starting composition during the storage or the casting operation can be prevented.

19 Claims, No Drawings

POLYMERIZATION REGULATORS AND COMPOSITIONS FOR RESIN

TECHNICAL FIELD

The present invention relates to a composition for resin suitable as a starting material for an optical material such as a plastic lens, prism, optical fiber, information recording medium, and filter, particularly, a plastic spectacle lens, and relates to a production method of the optical material.

BACKGROUND ART

Plastic materials have been widely used in various optical applications, particularly in manufacturing spectacle lenses, because of their light weight, toughness and easiness of dyeing. Optical products, particularly spectacle lenses are required to have, in addition to a low specific gravity, a high clearness, a low yellowness, optical properties such as a high refractive index and a large Abbe's number and physical properties such as high heat resistance and large mechanical strength. A large refractive index can decrease thickness of a lens. A large Abbe's number is important to avoid chromatic aberration of a lens. A high heat resistance and a large mechanical strength are important to facilitate fabrication and also for safety.

The inventors found a novel episulfide compound capable of providing a thin optical material which shows little chromatic aberration and has a refractive index of 1.7 or more and Abbe's number of 35 or more, as disclosed in Japanese Patent Application Laid-Open Nos. 9-71580, 9-110979, and 9-255781. The proposed episulfide compound, however, tends to increase its viscosity by spontaneous polymerization during the storage or injection operation because of a high reactivity of the episulfide group. The viscosity increase by the spontaneous polymerization becomes considerable, particularly, after the addition of a polymerization catalyst, thereby making it difficult to perform a long-term molding process. The episulfide compound is cured generally by ion polymerization. The polymerization rate of ion polymerization is difficult to control. Therefore, particularly in the production of a resin for optical material, optical distortion, striae, coloring, separation from mold during polymerization, etc. are likely to occur to reduce the yield of product.

DISCLOSURE OF INVENTION

A first object of the present invention is to provide a polymerization regulator which makes it easy to control the polymerization rate of an episulfide compound having, in one molecule, at least one epithio structure represented by the following Formula 2:

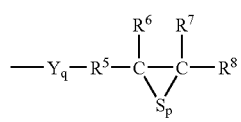

wherein $R^5$ is C1–C10 hydrocarbylene or single bond, $R^6$, $R^7$ and $R^8$ are each independently C1–C10 hydrocarbyl or hydrogen, Y is O, S, Se or Te, p is an integer from 1 to 5, and q is an integer from 0 to 5, thereby enhancing the uniformity of a resultant polymer.

A second object of the present invention is to enhance the stability of the episulfide compound, thereby preventing the viscosity increase during storing and during the casting process. Particularly, the present invention is intended to provide a composition which can produce a resin with a high refractive index and a high Abbe's number by preventing the viscosity increase due to spontaneous polymerization after adding a polymerization catalyst and by facilitating the molding operation.

As a result of intensive study for solving the above problems, the inventors have found that the polymerization rate of the episulfide compound having the epithio structure of Formula 2 can be suitably controlled by a compound represented by the following Formula 1:

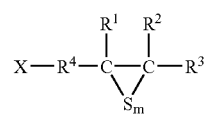

wherein $R^1$, $R^2$ and $R^3$ are each C1–C10 hydrocarbyl or hydrogen; $R^4$ is C1–C10 hydrocarbylene or single bond; X is F, Cl, Br, I, As, SH, OH, C1–C10 alkoxyl, C1–C10 alkylthio, or C1–C10 mercaptoalkylthio; and m is an integer from 1 to 5.

The inventors have further found that the viscosity increase during storing and during casting operation, particularly, the viscosity increase due to spontaneous polymerization after adding a polymerization catalyst can be prevented by compounding a halide of a 13–16 group element of the long periodic table into the episulfide compound having the epithio structure of Formula 2.

Thus, in a first aspect of the present invention, there is provided a polymerization regulator for controlling the polymerization rate of an episulfide compound having, in one molecule, at least one epithio structure represented by the following Formula 2:

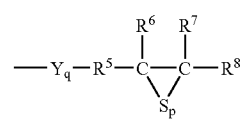

wherein $R^5$ to $R^8$, Y, p, and q are as defined above, the polymerization regulator being represented by the following Formula 1:

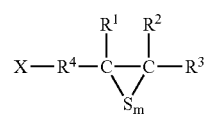

wherein $R^1$ to $R^4$, X and m are as defined above.

The effect of the polymerization regulator is remarkable when the episulfide compound has two or more epithio structures represented by the following Formula 3:

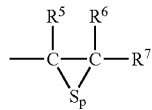

(3)

wherein $R^6$ to $R^8$ and p are as defined above, and more remarkable when the episulfide compound is represented by the following Formula 4:

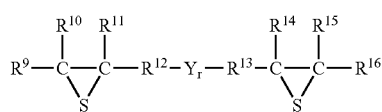

(4)

wherein $R^{12}$ and $R^{13}$ are each C1–C10 hydrocarbylene or single bond, $R^9$ to $R^{11}$ and $R^{14}$ to $R^{16}$ are each C1–C10 hydrocarbyl or hydrogen, Y is O, S, Se or Te, and r is an integer from 1 to 5.

In a second aspect of the present invention, there is provided a resin composition comprising an episulfide compound having, in one molecule, at least one epithio structure represented by Formula 2, and the polymerization regulator and/or a halide (halogen-containing stabilizer) of a 13–16 group element of the long periodic table. A halogen compound of silicon, germanium, tin or antimony is particularly preferable.

In a third aspect of the present invention, there is provided a method of producing a resin for optical material comprising a step of polymerizing the episulfide compound having, in one molecule, at least one epithio structure represented by Formula 2 in the presence of the halide of a 13–16 group element of the long periodic table and/or the polymerization regulator of the Formula 1.

BEST MODE FOR CARRYING OUT THE INVENTION

I Polymerization Regulator

The polymerization regulator for the episulfide compound is represented by the following Formula 1:

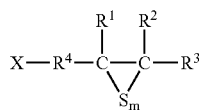

(1)

$R^1$, $R^2$ and $R^3$ are each C1–C10 hydrocarbyl or hydrogen, preferably $CH_3$ or H. $R^4$ is C1–C10 hydrocarbylene or single bond, preferably $CH_2$. X is F, Cl, Br, I, As, SH, OH, C1–C10 alkoxyl, C1–C10 alkylthio, or C1–C10 mercaptoalkylthio, preferably SH, $CH_3O$ or Cl. "m" is an integer form 1 to 5, preferably 1 or 2.

Examples of the compound of Formula 1 include, mercaptomethyl thiirane, methylthiomethyl thiirane, ethylthi-
omethyl thiirane, 2-mercaptoethylthiomethyl thiirane, methoxymethyl thiirane, ethoxymethyl thiirane, chloromethylthiirane, bromometyl thiirane, and iodomethyl thiirane, with mercaptomethyl thiirane, methoxymethyl thiirane, chloromethyl thiirane and bromomethyl thiirane being preferred, although not limited thereto. The above compound may be used alone or in combination of two or more. The polymerization regulator is suitably selected depending on the type of the episulfide compound. The amount of use of the polymerization regulator depends on the type of the episulfide compound and the polymerization conditions, and generally 0.0001 to 1 part by weight, preferably 0.001 to 0.5 part by weight based on 100 parts by weight of the episulfide compound. The amount of use of the polymerization regulator referred to herein means an amount present in the reaction system at the initiation of reaction, and the amount of the polymerization regulator during the polymerization or after the polymerization is not necessarily needed to be within the above range.

II Halogen-containing Stabilizer

In the present invention, a halide of 13–16 group element of the long periodic table is used as a stabilizer for the episulfide compound.

The halogen-containing stabilizer includes any halide of a 13–16 group element of the long periodic table. Examples thereof include chlorides such as aluminum chloride, indium chloride, thallium chloride, phosphorus trichloride, phosphorus pentachloride, and bismuth chloride, and halides derived from the preceding chlorides by replacing their chlorine entirely or partly with fluorine, bromine or iodine; compounds having halogen and hydrocarbon radical such as diphenylchloroboron, phenyldichloroboron, diethylchlorogallium, dimethylchloroindium, diethylchlorothallium, diphenylchlorothallium, ethyldichlorophosphine, butyldichlorophosphine, triphenylphosphine dichloride, diphenylchloroarsenic, tetraphenylchloroarsenic, diphenyldichloroselenium, phenylchloroselenium, and diphenyldichlorotellurium, and compounds derived from the preceding compounds by replacing their chlorine entirely or partly with fluorine, bromine or iodine; halogenated hydrocarbons such as chlorophenol, dichlorophenol, trichlorophenol, chloroaniline, dichloroaniline, chloronitorobenzene, dichloronitrobenzene, chlorobenzene, dichlorobenzene, trichlorobenzen, chloroacetophenone, chlorotoluene, chloronitoroaniline, chlorbenzyl cyanide, chlorobenzaldehyde, chlorobenzotrichloride, chloronaphthalene, dichloronaphthalene, chlorothiophenol, dichlorothiophenol, methacryl chloride, benzyl chloride, chlorobenzyl chloride, chloroacetic acid, dichloroacetic acid, trichloroacetic acid, chlorosuccinic acid, oxaloyl dichloride,triglycol dichloride, methansulfonyl chloride, chlorobenzoic acid, chlorosalicylic acid, 4,5-dichlorophthalic acid, 3,5-dichlorosalicylic acid, isopropyl chloride, acryl chloride, epichlorohydrin, chloromethyl thiirane, propylenechlorohydrin, chloranil, dichlorodicyanobenzoquinone, dichlorophene, dichloro-1,4-benzoquinone, dichlorobenzophenone, N-chlorophtalimide, 1,3-dichloro-2-propanol, methyl 2,3-dichloropropionate, p-chlorobenzenesulfonic acid, ethyl 2-chloropropionate, dichloromethane, chloroform, and carbon tetrachloride; acid chlorides such as benzoyl chloride, phthaloyl chloride, isophthaloyl chloride, terephthaloyl chloride, methacryloyl chloride, succinyl chloride, fumaroyl chloride, niconinoyl chloride, chloroniconinoyl chloride, oleoyl chloride, benzoyl chloride, chlorobenzoyl chloride, and propionyl chloride; and compounds derived from the preceding organic halide by replacing their chlorine entirely or partly with fluorine, bromine or iodine.

A more preferred halogen-containing stabilizer is a halide of silicon, germanium, tin or antimony represented by the following Formula 5:

$$R^{17}_s MX^2_t \tag{5}$$

In the above formula, $R^{17}$ is C1–C8 alkyl, C1–C4 alkoxyl or phenyl. M is silicon, germanium, tin or antimony. $X^2$ is halogen such as fluorine, chlorine, bromine and iodine, halogenated alkyl, halogenated alkenyl, halogenated alkoxyl, or halogenated aryl. "s" is an integer including zero, and "t" is an integer of 1 or more, with s+t being equal to the valency of M. When "s" is an integer of two or more, a plurality of $R^{17}$ groups may be the same or different.

Examples of halides of silicon include silicon tetrachloride, methyltrichlorosilane, dimethyldichlorosilane, trimethylchlorosilane, ethyltrichlorosilane, diethyldichlorosilane, triethylchlorosilane, propyltrichlorosilane, dipropyldichlorosilane, tripropylchlorosilane, n-butyltrichlorosilane, di-n-butyldichlorosilane, tri-n-butylchlorosilane, t-butyltrichlorosilane, di-t-butyldichlorosilane, tri-t-butylchlorosilane, octyltrichlorosilane, dioctyldichlorosilane, trioctylchlorosilane, phenyltrichlorosilane, diphenyldichlorosilane, triphenylchlorosilane, allylchlorodimethylsilane, trichloroallylsilane, t-butylchlorodimethylsilane, diphenyl-t-butylchlorosilane, t-butoxychlorodiphenylsilane, trimethyl(2-chloroallyl)silane, trimethylchloromethylsilane, n-butyl-chlorodimethylsilane, and compounds derived from the preceding compounds by replacing their chlorine entirely or partly with fluorine, bromine or iodine.

Examples of halides of germanium include germanium tetrachloride, methylgermanium trichloride, dimethylgermanium dichloride, trimethylgermanium chloride, ethylgermanium trichloride, diethylgermanium dichloride, triethylgermanium chloride, propylgermanium trichloride, dipropylgermanium dichloride, tripropylgermanium chloride, n-butylgermanium trichloride, di-n-butylgermanium dichloride, tri-n-butylgermanium chloride, t-butylgermanium trichloride, di-t-butylgermanium dichloride, tri-t-butylgermanium chloride, amylgermanium trichloride, diamylgermanium dichloride, triamylgermanium chloride, octylgermanium trichloride, dioctylgermanium dichloride, trioctylgermanium chloride, phenylgermanium trichloride, diphenylgermanium dichloride, triphenylgermanium chloride, tolylgermanium trichloride, ditolylgermanium dichloride, tritolylgermanium chloride, benzylgermanium trichloride, dibenzylgermanium dichloride, tribenzylgermanium chloride, cyclohexylgermanium trichloride, dicyclohexylgermanium dichloride, tricyclohexylgermanium chloride, vinylgermanium trichloride, divinylgermanium dichloride, trivinylgermanium chloride, allyltrichlorogermane, bis(chloromethyl)dimethylgermane, chloromethyltrichlorogermane, t-butyldimethylchlorogermane, carboxyethyltrichlorogermane, chloromethyltrimethylgermane, dichloromethyltrimethylgermane, 3-chloropropyltrichlorogermane, phenyldimethylchlorogermane, 3-(trichlorogermyl)propionyl chloride, and compounds derived from the preceding compounds by replacing their chlorine entirely or partly with fluorine, bromine or iodine.

Examples of halides of tin include tin tetrachloride, diethyldichlorosilane, dimethyltin dichloride, trimethyltin chloride, ethyltin trichloride, diethyltin dichloride, triethyltin chloride, propyltin trichloride, dipropyltin dichloride, tripropyltin chloride, n-butyltin trichloride, di-n-butyltin dichloride, tri-n-butyltin chloride, t-butyltin trichloride, di-t-butyltin dichloride, tri-t-butyltin chloride, amyltin trichloride, diamyltin dichloride, triamyltin chloride, octyltin trichloride, dioctyltin dichloride, trioctyltin chloride, phenyltin trichloride, diphenyltin dichloride, triphenyltin chloride, tolyltin trichloride, ditolyltin dichloride, tritolyltin chloride, benzyltin trichloride, dibenzyltin dichloride, tribenzyltin chloride, cyclohexyltin trichloride, dicyclohexyltin dichloride, tricyclohexyltin chloride, vinyltin trichloride, divinyltin dichloride, trivinyltin chloride, butylchlorodihydroxytin, bis(2,4-pentadionato)dichlorotin, carbomethoxyethyltrichlorotin, chloromethyltrimethyltin, diallyldichlorotin, dibutylbutoxychlorotin, tri-n-pentylchlorotin, and compounds derived from the preceding compounds by replacing their chlorine entirely or partly with fluorine, bromine or iodine.

Examples of halides of antimony include antimony pentachloride, methylantimony tetrachloride, dimethylantimony trichloride, trimethylantimony dichloride, tetramethylantimony chloride, ethylantimony tetrachloride, diethylantimony trichloride, triethylantimony dichloride, tetraethylantimony chloride, butylantimony tetrachloride, dibutylantimony trichloride, tributylantimony dichloride, tetrabutylantimony chloride, phenylantimony tetrachloride, diphenylantimony trichloride, triphenylantimony dichloride, tetraphenylantimony chloride, and compounds derived from the preceding compounds by replacing their chlorine entirely or partly with fluorine, bromine or iodine.

It should be noted, however, that the halogen-containing stabilizer is not limited thereto, and the compounds cited above may be used alone or in combination of two or more. The halogen-containing stabilizer is preferably chlorides, more preferably dichlorides and trichlorides, and still more preferably dichlorides and trichlorides of alkyl germanium, alkyl tin and alkyl antimony. Examples of the most preferred halogen-containing stabilizer include dibutyltin dichloride, butyltin trichloride, dioctyltin dichloride, octyltin trichloride, dibutyldichlorogermanium, butyltrichlorogermanium, diphenyldichlorogermanium, phenyltrichlorogermanium, and triphenylantimony dichloride.

The addition amount of the halogen-containing stabilizer is 0.001 to 10 parts by weight, preferably 0.01 to 1 part by weight based on 100 parts by weight of the episulfide compound. The addition amount is determined according to the types of the episulfide compound and the halogen-containing stabilizer. When two or more kinds of episulfide compounds are used, it is preferred to regulate the addition amount depending on the mixing ratio and the types of the episulfide compounds. A known stabilizer for the episulfide compound may be used combinedly as far as it does not adversely affect the effect of the present invention.

III Episulfide Compound

The episulfide compound used in the present invention shows a high refractive index and a high Abbe's number well balanced each other when made into an optical material, and has, in one molecule, at least one epithio structure represented by the following Formula 2:

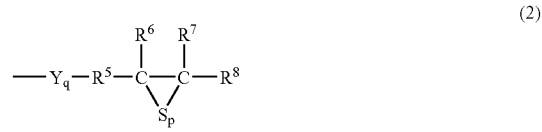

wherein $R^5$ to $R^8$, Y, p, and q are as defined above.

To obtain a cured resin with a high refractive index, $R^5$ is preferably single bond or C1–C2 hydrocarbyl, and $R^6$, $R^7$ and $R^8$ are each preferably hydrogen or methyl. More preferably, $R^5$ is single bond or methylene, and $R^6$, $R^7$ and $R^8$ are each hydrogen.

The effect of the polymerization regulator becomes more remarkable when the episulfide compound has two or more epithio structures represented by the following Formula 3:

$$\begin{array}{c} R^5 \ R^6 \\ | \ \ | \\ -C-C-R^7 \\ \diagdown / \\ S_p \end{array} \quad (3)$$

wherein $R^6$ to $R^8$ and p are as defined above, and still more remarkable when the episulfide compound is represented by the following Formula 4:

$$R^9-\underset{\underset{S}{\diagdown/}}{\overset{R^{10} \ R^{11}}{C-C}}-R^{12}-Y_r-R^{13}-\underset{\underset{S}{\diagdown/}}{\overset{R^{14} \ R^{15}}{C-C}}-R^{16} \quad (4)$$

wherein $R^{12}$ to $R^{16}$, Y, and r are as defined above.

The episulfide compound include any compounds having, in one molecule, at least one epithio structure represented by Formula 2. The episulfide compound will be described below in more detail by classifying into the following groups A to E.

A: Compounds having, in one molecule, at least one epithio structure wherein n=0 (epithio group or epithioalkyl group).
B: Compounds having, in one molecule, at least one epithio structure wherein Y=O (epithioalkyloxy group).
C: Compounds having, in one molecule, at least one epithio structure wherein Y=S (epithioalkylthio group).
D: Compounds having, in one molecule, at least one epithio structure wherein Y=Se (epithioalkylseleno group).
E: Compounds having, in one molecule, at least one epithio structure wherein Y=Te (epithioalkyltelluro group).

The episulfide compounds A to E are mainly constituted by, in addition to the epithio structure, an aliphatic chain backbone, an aliphatic branched backbone, an alicyclic backbone, an aromatic backbone or a heterocyclic backbone having nitrogen, oxygen, sulfur, selenium or tellurium as the heteroatom. The episulfide compound may have two or more of these backbone structures, and also, may simultaneously have two or more of epithio group, epithioalkyloxy group, epithioalkylthio group, epithioalkylseleno group and epithioalkyltelluro group. The episulfide compound may also have a sulfide linkage, a selenide linkage, a telluride linkage, an ether linkage, a sulfone linkage, a ketone linkage, an ester linkage, an amide linkage or a urethane linkage in the molecule.

Preferred examples of the compounds A (n=0) include:
A-1: Compounds having aliphatic chain backbone
bis(βepithioethyl)sulfide, bis(β-epithioethyl)disulfide, 1,1-bis(epithioethyl)methane, 1,1-bis(epidithioethyl)methane, 1-(epithioethyl)-1-(β-epithiopropyl)methane, 1,1-bis(β-epithiopropyl)methane, 1-(epithioethyl)-1-(β-epithiopropyl)ethane, 1,2-bis(β-epithiopropyl)ethane, 1,2-bis(β-epidithiopropyl)ethane, 1-(epithioethyl)-3-(β-epithiopropyl)butane, 1,3-bis(β-epithiopropyl)propane, 1-(epithioethyl)-4-(β-epithiopropyl)pentane, 1,4-bis(β-epithiopropyl)butane, 1-(epithioethyl)-5-(β-epithiopropyl)hexane, 1-(epithioethyl)-2-(γ-epithiobutylthio)ethane, 1-(epithioethyl)-2-[2-(γ-epithiobutylthio)ethylthio]ethane, tetrakis(β-epithiopropyl)methane, 1,1,1-tris(β-epithiopropyl)propane, 1,3-bis(β-epithiopropyl)-1-(β-epithiopropyl)-2-thiapropane and 1,5-bis(β-epithiopropyl)-2,4-bis(β-epithiopropyl)-3-thiapentane;

A-2: Compounds having alicyclic backbone
1,3- or 1,4-bis(epithioethyl)cyclohexane, 1,3- or 1,4-bis(β-epithiopropyl)cyclobexane, bis[4-(epithioethyl)cyclohexyl]methane, bis[4-(β-epithiopropyl)cyclohexyl]methane, 2,2-bis[4-(epithioethyl)-cyclohexyl]propane, 2,2-bis[4-(β-epithiopropyl)cyclohexyl]propane, bis[4-(β-epithiopropyl)cyclohexyl] sulfide, bis[4-(epithioethyl)cyclohexyl] sulfide, 2,5-bis(epithioethyl)-1,4-dithiane, 2,5-bis(β-epithiopropyl)-1,4-dithiane, 4-epithioethyl-1,2-cyclohexene sulfide, 4-epoxy-1,2-cyclohexene sulfide, 2,3-, 2,5- or 2,6-bis(1,2-epithioethyl)-1,4-diselenane, 2,3-, 2,5- or 2,6-bis(2,3-epithiopropyl)-1,4-diselenane, 2,4-, 2,5- or 2,6-bis(1,2-epithioethyl)-1,3-diselenane, 2,4-, 2,5- or 2,6-bis(2,4-epithiopropyl)-1,3-diselenane, 2,3-, 2,5-, 2,6- or 3,5-bis(1,2-epithioethyl)-1-thia-4-selenane, 2,3-, 2,5-, 2,6- or 3,5-bis(2,3-epithiopropyl)-1-thia-4-selenane, 2,4- or 4,5-bis(1,2-epithioethyl)-1,3-diselenolane, 2,4- or 4,5-bis(2,4-epithiopropyl)-1,3-diselenolane, 2,4-, 2,5- or 4,5-bis(1,2-epithioethyl)-1-thia-3-selenolane, 2,4-, 2,5- or 4,5-bis(2,4-epithiopropyl)-1-thia-3-selenolane, 2,3-, 2,4-, 2,5- or 3,4-bis(1,2-epithioethyl)selenophane, 2,3-, 2,4-, 2,5- or 3,4-bis(2,3-epithiopropyl)selenophane, 2,3-, 2,5-, 2,6-bis(1,2-epithioethyl)-1,4-ditellurane, 2,3-, 2,5- or 2,6-bis(2,3-epithiopropyl)-1,4-ditellurane, 2,4-, 2,5- or 2,6-bis(1,2-epithioethyl)-1,3-ditellurane, 2,4-, 2,5- or 2,6-bis(2,4-epithiopropyl)-1,3-ditellurane, 2,3-, 2,5-, 2,6- or 3,5-bis(1,2-epithioethyl)-1-thia-4-tellurane, 2,3-, 2,5-, 2,6- or 3,5-bis(2,3-epithiopropyl)-1-thia-4-tellurane, 2,4- or 4,5-bis(1,2-epithioethyl)-1,3-ditellurolane, 2,4- or 4,5-bis(2,4-epithiopropyl)-1,3-ditellurolane, 2,4-, 2,5- or 4,5-bis(1,2-epithioethyl)-1-thia-3-tellurolane, 2,4-, 2,5- or 4,5-bis(2,4-epithiopropyl)-1-thia-3-tellurolane, 2,3-, 2,4-, 2,5- or 3,4-bis(1,2-epithioethyl)tellurophane, and 2,3-, 2,4-, 2,5- or 3,4-bis(2,3-epithiopropyl)tellurophane;

A-3: Compounds having aromatic backbone
1,3- or 1,4-bis(epithioethyl)benzene, 1,3- or 1,4-bis(β-epithiopropyl)benzene, bis[4-(epithioethyl)phenyl]methane, bis[4-(β-epithiopropyl)phenyl]methane, 2,2-bis[4-(epithioethyl)phenyl]propane, 2,2-bis[4-(β-epithiopropyl)phenyl]propane, bis[4-(epithioethyl)phenyl] sulfide, bis[4-(β-epithiopropyl)phenyl] sulfide, bis[4-(epithioethyl)phenyl] sulfone, bis[4-(β-epithiopropyl)phenyl] sulfone, 4,4'-bis(epithioethyl)biphenyl, and 4,4'-bis(β-epithiopropyl)biphenyl; and A-4: Compounds obtained by replacing at least one hydrogen of the epithio group in the compounds A-1 to A-3 with methyl.

Preferred examples of the compounds B (Y=O) include:
B-1: Compounds having aliphatic chain backbone
bis(β-epithiopropyl)ether, bis(β-epidithiopropyl)ether, bis(β-epithiopropyloxy)methane, 1,2-bis(β-epithiopropyloxy)ethane, 1,3-bis(β-epithiopropyloxy)propane, 1,2-bis(β-epithiopropyloxy)propane, 1-(β-epithiopropyloxy)-2-(β-epithiopropyloxymethyl)propane, 1,4-bis(β-epithiopropyloxy)butane, 1,3-bis(β-epithiopropyloxy)butane, 1-(β-epithiopropyloxy)-3-(β- epithiopropyloxymethyl)butane, 1,5-bis(β-epithiopropyloxy)pentane, 1-(β-epithiopropyloxy)-4-(β-epithiopropyloxymethyl)pentane, 1,6-bis(β-epithiopropyloxy)hexane, bis(epithioethyl)ether, 1-(β-epithiopropyloxy)-5-(β-epithiopropyloxymethyl)hexane, 1-(β-epithiopropyloxy)-2-[(2-β-epithiopropyloxyethyl)oxy]ethane, 1-(β-epithiopropyloxy)-2-[[2-(2-β-epithiopropyloxyethyl)oxyethyl]oxy]ethane, bis(5,6-epithio-3-oxahexyl)selenide, bis(5,6-epithio-3-oxahexyl)telluride, tetrakis(β-epithiopropyloxymethyl)methane, 1,1,1-tris(β-epithiopropyloxymethyl)propane, 1,5-bis(β-epithiopropmoxy)-2-(β-epithiropopyloxyrethyl)-3-thiapentane, 1,5-bis(β-epithiopropyloxy)-2,4-bis(β-epithiopropyloxymethyl)-3-thiapentane, 1-(β-epithiopropyloxy)-2,2-bis(β-epithiopropyloxymethyl)-4-thiahexane, 1,5,6-tris(β-epithiopropyloxy)-4-(β-epithiopropyloxymethyl)-3-thiahexane, 1,8-bis(β-epithiopropyloxy)-4-(β-epithiopropyloxymethyl)-3,6-dithiaoctane, 1,8-bis(β-epithiopropyloxy)-4,5-bis(β-epithiopropyloxymethyl)-3,6-dithiaoctane, 1,8-bis(β-epithiopropyloxy)-4,4-bis(β-epithiopropyloxymethyl)-3,6-dithiaoctane, 1,8-bis(β-epithiopropyloxy)-2,4,5-tris(β-epithiopropyloxymethyl)-3,6-dithiaoctane, 1,8-bis(β-epithiopropyloxy)-2,5-bis(β-epithiopropyloxymethyl)-3,6-dithiaoctane, 1,9-bis(β-epithiopropyloxy)-5-(β-epithiopropyloxymethyl)-5-[(2-β-epithiopropyloxyethyl)oxymethyl]-3,7-dithianonane, 1,10-bis(β-epithiopropyloxy)-5,6-bis[(2-β-epithiopropyloxyethyl)oxy]-3,6,9-trithiadecane, 1,11-bis(β-epithlopropyloxy)-4,8-bis(β-epithlopropyloxymethyl)-3,6,9-trithiaundecane, 1,11-bis(β-epithiopropyloxy)-5,7-bis(β-epithiopropyloxymethyl)-3,6,9-trithiaundecane, 1,11-bis(β-epithiopropyloxy)-5,7-[(2-β-epithiopropyloxyethyl)oxymethyl]-3,6,9-trithiaundecane, and 1,11-bis(β-epithiopropyloxy)-4,7-bis(β-epithiopropyloxymethyl)-3,6,9-trithiaundecane;

B-2: Compounds having alicyclic backbone 1,3- or 1,4-bis(β-epithiopropyloxy)cyclohexane, 1,3- or 1,4-bis(β-epithiopropyloxymethyl)cyclohexane, bis[4-(β-epithiopropyloxy)cyclohexyl]methane, 2,2-bis[4-(β-epithiopropyloxy)cyclohexyl]propane, bis[4-(β-epithiopropyloxy)cyclohexyl] sulfide, 2,5-bis(β-epithiopropyloxymethyl)-1,4-dithiane, 2,5-bis(β-epithiopropyloxyethyloxymethyl)-1,4-dithiane, 2,4- or 4,5-bis(3,4-epithio-1-oxabutyl)-1,3-diselenolane, 2,4- or 4,5-bis(4,5-epithio-2-oxapentyl)-1,3-diselenolane, 2,4-, 2,5- or 4,5-bis(3,4-epithio-1-oxabutyl)-1-thia-3-selenolane, 2,4-, 2,5- or 4,5-bis(4,5-epithio-2-oxapentyl)-1-thia-3-selenolane, bis(3,4-epithio-1-oxabutyl)tricycloselenaoctane, bis(3,4-epithio-1-oxabutyl)dicycloselenanonane, 2,3-, 2,4-, 2,5- or 3,4-bis(3,4-epithio-1-oxabutyl)selenophane, 2,3-, 2,4-, 2,5- or 3,4-bis(4,5-epithio-2-oxapentyl)selenophane, 2,3-, 2,5- or 2,6-bis(3,4-epithio-1-oxabutyl)-1,4-diselenane, 2,3-, 2,5- or 2,6-bis(4,5-epithio-2-oxapenyyl)-1,4-diselenane, 2,4-, 2,5- or 2,6-bis(3,4-epithio-1-oxabutyl)-1,3-diselenane, 2,4-, 2,5- or 2,6-bis(4,5-epithio-2-oxapentyl)-1,3-diselenane, 2,3-, 2,5-, 2,6- or 3,5-bis(3,4-epithio-1-oxabutyl)-1-thia-4-selenane, 2,3-, 2,5-, 2,6- or 3,5-bis(4,5-epithio-2-oxapentyl)-1-thia-4-selenane, 2,4- or 4,5-bis(3,4-epithio-1-oxabutyl)-1,3-ditellurolane, 2,4- or 4,5-bis(4,5-epithio-2-oxapentyl)-1,3-ditellurolane, 2,4-, 2,5- or 4,5-bis(3,4-epithio-1-oxabutyl)-1-thia-3-tellurolane, 2,4-, 2,5- or 4,5-bis(4,5-epithio-2-oxapentyl)-1-thia-3-tellurolane, bis(3,4-epithio-1-oxabutyl)tricycloteluraoctane, bis(3,4-epithio-1-oxabutyl)dicycloteluranonane, 2,3-, 2,4-, 2,5- or 3,4-bis(3,4-epithio-1-oxabutyl)tellurophane, 2,3-, 2,4-, 2,5- or 3,4-bis(4,5-epitho-2-oxapentyl)tellurophane, 2,3-, 2,5- or 2,6-bis(3,4-epithio-1-oxabutyl)-1,4-ditellurane, 2,3-, 2,5- or 2,6-bis(4,5-epithio-2-oxapentyl)-1,4-ditellurane, 2,4-, 2,5- or 2,6-bis(3,4-epithio-1-oxabutyl)-1,3-ditellurane, 2,4-, 2,5- or 2,6-bis(4,5-epithio-2-oxapentyl)-1,3-ditellurane, 2,3-, 2,5-, 2,6- or 3,5-bis(3,4-epithio-1-oxabutyl)-1-thia-4-tellurane, and 2,3-, 2,5-, 2,6- or 3,5-bis(4,5-epithio-2-oxapentyl)-1-thia-4-tellurane;

B-3: Compounds having aromatic backbone 1,3- or 1,4-bis(β-epithiopropyloxy)benzene, 1,3- or 1,4-bis(β-epithiopropyloxymethyl)benzene, bis[4-(β-epithiopropyl)phenyl]methane, 2,2-bis[4-(β-epithiopropylthio)phenyl]propane, bis[4-(β-epithiopropylthio)phenyl] sulfide, bis[4-(β-epithiopropylthio)phenyl] sulfone, and 4,4'-bis(β-epithiopropylthio)biphenyl; and B-4: Compounds obtained by replacing at least one hydrogen of the epithio group in the compounds B-1 to B-3 with methyl.

Preferred examples of the compounds C (Y═S) are epoxy compounds derived from a mercapto-containing compound and an epihalohydrin, with its epoxyalkylthio group (specifically, β-epoxypropylthio group) replaced by epithioalkylthio group. Specific examples are recited below.

C-1: Compounds having aliphatic chain backbone bis(β-epithiopropyl)sulfide, bis(β-epidithiopropyl)sulfide, bis(β-ethiopropyl)disulfide, bis(β-epidithiopropyl)disulfide, bis(β-epithiopropyl) trisulfide, bis(β-epithiopropylthio)methane, 1,2-bis(β-epithiopropylthio)ethane, 1,3-bis(β-epithiopropylthio)propane, 1,2-bis(β-epithiopropylthio)propane, bis(epithioethyl)sulfide, 1-(β-epithiopropylthio)-2-(β-epithiopropylthiomethyl)propane, 1,2,3-tris(β-epithiopropylthio)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,5-bis(β-epithiopropylthio)-2-(β-epithiopropylthiomethyl)-3-thiapentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-β-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(β-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis(β-epithiopropylthiomethyl)-3,6-dithiaoctane, 1,8-bis(β-epithiopropylthio)-4,4-bis(β-epithiopropylthiomethyl)-3,6-dithiaoctane, 1,8-bis(β-epithiopropylthio)-2,4,5-tris(β-epithiopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,11-bis(β-epithiopropylthio)-5,7-[(2-β-epithiopropylthioethyl)thiomethyl]-3,6,9-trithiaundecane, 1,11-bis(β-epithiopropylthio)-4,7-bis(β-epithiopropylthiomethyl)-3,6,9-trithiaundecane, tetra[2-(β-epithiopropylthio)

acetylmethyl]methane, 1,1,1-tri[2-(β-epithiopropylthio) acetylmethyl]propane, tetra [2-(β-epithiopropylthiomethyl) acetylmethyl]methane, 1,1,1-tri[2-(β-epithiopropylthiomethyl)acetylmethyl]propane, bis(5,6-epithio-3-thiahexyl) selenide, 2,3-bis(6,7-thioepoxy-1-selena-4-thiaheptyl)-1-(3,4-thioepoxy-1-thiabutyl)propane, 1,1,3,3-tetrakis(4,5-thioepoxy-2-thiapentyl)-2-selenapropane, bis(4,5-thioepoxy-2-thiapentyl)-3,6,9-triselenaundecane-1,11-bis(3,4-thioepoxy-1-thiabutyl), 1,4-bis(3,4-thioepoxy-1-thiabutyl)-2,3-bis(6,7-thioepoxy-1-selena-4-thiaheptyl)butane, tris(4,5-thioepoxy-2-thiapentyl)-3-selena-6-thiaoctane-1,8-bis(3,4-thioepoxy-1-thiabutyl), bis(5,6-epithio-3-thiahexyl)telluride, 2,3-bis(6,7-thioepoxy-1-tellura-4-thiaheptyl)-1-(3,4-thioepoxy-1-thiabutyl)proane, 1,1,3,3-tetrakis(4,5-thioepoxy-2-thiapentyl)-2-tellurapropane, bis(4,5-thioepoxy-2-thiapentyl)-3,6,9-tritelleraundecane-1,11-bis(3,4-thioepoxy-1-thiabutyl), 1,4-bis(3,4-thioepoxy-1-thiabutyl)-2,3-bis(6,7-thioepoxy-1-tellura-4-thiaheptyl)butane and tris(4,5-thioepoxy-2-thiapentyl)-3-tellura-6-thiaoctane-1,8-bis(3,4-thioepoxy-1-thiabutyl);

C-2: Compounds having alicyclic backbone 1,3- or 1,4-bis(β-epithiopropylthio)cyclohexane, 1,3- or 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl] sulfide, 2,5-bis(β-epithiopropylthiomethyl)-1,4-dithiane, 2,5-bis(β-epithiopropylthioethylthiomethyl)-1,4-dithiane, 2,3-, 2,5- or 2,6-bis(3,4-epithio-1-thiabutyl)-1,4-diselenane, 2,3-, 2,5- or 2,6-bis(4,5-epithio-2-thiapentyl)-1,4-diselenane, 2,4-, 2,5- or 5,6-bis(3,4-epithio-1-thiabutyl)-1,3-diselenane, 2,4-, 2,5- or 5,6-bis(4,5-epithio-2-thiapentyl)-1,3-diselenane, 2,3-, 2,5-, 2,6- or 3,5-bis(3,4-epithio-1-thiabutyl)-1-thia-4-selenane, 2,3-, 2,5-, 2,6- or 3,5-bis(4,5-epithio-2-thiapentyl)-1-thia-4-selenane, 2,4- or 4,5-bis(3,4-epithio-1-thiabutyl)-1,3-diselenolane, 2,4- or 4,5-bis(4,5-epithio-2-thiapentyl)-1,3-diselenolane, 2,4-, 2,5- or 4,5-bis(3,4-epithio-1-thiabutyl)-1-thia-3-selenolane, 2,4-, 2,5- or 4,5-bis(4,5-epithio-2-thiapentyl)-1-thia-3-selenolane, 2,6-bis(4,5-epithio-2-thiapentyl)-1,3,5-triselenane, bis(3,4-epithio-1-thiabutyl) tricycloselenaoctane, bis(3,4-epithio-1-thiabutyl) dicycloselenanonane, 2,3-, 2,4-, 2,5- or 3,4-bis(3,4-epithio-1-thiabutyl)selenophane, 2,3-, 2,4-, 2,5- or 3,4-bis(4,5-epithio-2-thiapentyl)selenophane, 2-(4,5-thioepoxy-2-thiapentyl)-5-(3,4-thioepoxy-1-thiabutyl)-1-selenacyclohexane, 2,3-, 2,4-, 2,5-, 2,6-, 3,4-, 3,5- or 4,5-bis(3,4-thioepoxy-1-thiabutyl)-1-selenacyclohexane, 2,3-, 2,4-, 2,5-, 2,6-, 3,4-, 3,5- or 4,5-bis(4,5-thioepoxy-2-thiapentyl)-1-selenacyclohexane, 2,3-, 2,5- or 2,6-bis(3,4-epithio-1-thiabutyl)-1,4-ditellurane, 2,3-, 2,5- or 2,6-bis(4,5-epithio-2-thiapentyl)-1,4-ditellurane, 2,4-, 2,5- or 5,6-bis(3,4-epithio-1-thiabutyl)-1,3-ditellurane, 2,4-, 2,5- or 5,6-bis(4,5-epithio-2-thiapentyl)-1,3-ditellurane, 2,3-, 2,5-, 2,6- or 3,5-bis(3,4-epithio-1-thiabutyl)-1-thia-4-tellurane, 2,3-, 2,5-, 2,6- or 3,5-bis(4,5-epithio-2-thiapentyl)-1-thia-4-tellurane, 2,4- or 4,5-bis(3,4-epithio-1-thiabutyl)-1,3-ditellurolane, 2,4- or 4,5-bis(4,5-epithio-2-thiapentyl)-1,3-ditellurolane, 2,4-, 2,5- or 4,5-bis(3,4-epithio-1-thiabutyl)-1-thia-3-tellurolane, 2,4-, 2,5- or 4,5-bis(4,5-epithio-2-thiapentyl)-1-thia-3-tellurolane, 2,6-bis(4,5-epithio-2-thiapentyl)-1,3,5-tritellurane, bis(3,4-epithio-1-thiabutyl) tricycloteluraoctane, bis(3,4-epithio-1-thiabutyl) dicycloteluranonane, 2,3-, 2,4-, 2,5- or 3,4-bis(3,4-epithio-1-thiabutyl)tellurophane, 2,3-, 2,4-, 2,5- or 3,4-bis(4,5-epithio-2-thiapentyl)tellurophane, 2-(4,5-thioepoxy-2-thiapentyl)-5-(3,4-thioepoxy-1-thiabutyl)-1-telluracyclohexane, 2,3-, 2,4-, 2,5-, 2,6-, 3,4-, 3,5- or 4,5-bis(3,4-thioepoxy-1-thiabutyl)-1-tellurac and 2,3-, 2,4-, 2,5-, 2,6-, 3,4-, 3,5- or 4,5-bis(4,5-thioepoxy-2-thiapentyl)-1-te C-3: Compounds having aromatic backbone 1,3- or 1,4-bis(β-epithiopropylthio)benzene, 1,3- or 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl] sulfone, and 4,4'-bis(β-epithiopropylthio)biphenyl; and C-4: Compounds obtained by replacing at least one hydrogen of the β-epithiopropyl group in the compounds B-1 to B-3 with methyl.

Preferred examples of the compounds D (Y=Se) are epoxy compounds with one or more epoxyalkylseleno groups (specifically, β-epoxypropylseleno group) replaced by epithioalkylseleno groups, the epoxy compounds being derived from an epihalohdrin and a selenium compound such as metallic selenium, alkali metal selenides, alkali metal selenols, alkyl selenols, aryl selenols and hydrogen selenide. Specific examples are recited below.

D-1: Compounds having aliphatic chain backbone bis(β-epithiopropyl)selenide, bis(β-epidithiopropyl)selenide, bis(β-epithiopropyl)diselenide, bis(β-epidithiopropyl)diselenide, bis(β-epithiopropyl) triselenide, bis(β-epithiopropylseleno)methane, 1,2-bis(β-epithiopropylseleno)ethane, 1,3-bis(β-epithiopropylseleno)propane, 1,2-bis(β-epithiopropylseleno)propane, bis(epithioethyl)selenide, bis(epithioethyl) diselenide, 1-(β-epithiopropylseleno)-2-(β-epithiopropylselenomethyl)propane, 1,2,3-tris(β-epithiopropylseleno)propane, 1,4-bis(β-epithiopropylseleno)butane, 1,3-bis(β-epithiopropylseleno)butane, 1-(β-epithiopropylseleno)-3-(β-epithiopropylselenomethyl)butane, 1,5-bis(β-epithiopropylseleno)pentane, 1-(β-epithiopropylseleno)-4-(β-epithiopropylselenomethyl)pentane, 1,5-bis(β-epithiopropylseleno)-2-(β-epithiopropylselenomethyl)-3-thiapentane, 1,6-bis(β-epithiopropylseleno)hexane, 1-(β-epithiopropylseleno)-5-(β-epithiopropylselenomethyl) hexane, 1-(β-epithiopropylseleno)-2-[(2-β-epithiopropylselenoethyl)thio]ethane, 1-(β-epithiopropylseleno)-2-[[2-(2-β-epithiopropylselenoethyl)selenoethyl]thio]ethane, tetrakis(β-epithiopropylselenomethyl)methane, 1,1,1-tris(β-epithiopropylselenomethyl)propane, 1,5-bis(β-epithiopropylseleno)-2-(β-epithiopropylselenomethyl)-3-thiapentane, 1,5-bis(β-epithiopropylseleno)-2,4-bis(β-epithiopropylselenomethyl)-3-thiapentane, 1-(β-epithiopropylseleno)-2,2-bis(β-epithiopropylselenomethyl)-4-thiahexane, 1,5,6-tris(β-epithiopropylseleno)-4-(β-epithiopropylselenomethyl)-3-thiahexane, 1,8-bis(β-epithiopropylseleno)-4-(β-epithiopropylselenomethyl)-3,6-dithiaoctane, 1,8-bis(β-epithiopropylseleno)-4,5-bis(β-epithiopropylselenomethyl)-3,6-dithiaoctane, 1,8-bis(β-epithiopropylseleno)-4,4-bis(β-epithiopropylselenomethyl)-3,6-dithiaoctane, 1,8-bis(β-epithiopropylseleno)-2,4,5-tris(β-epithiopropylselenomethyl)-3,6-dithiaoctane, 1,8-bis(β-epithiopropylseleno)-2,5-bis(β-epithiopropylselenomethyl)-3,6-dithiaoctane, 1,9-bis(β-epithopropylseleno)-5-(β-epithiopropylselenomethyl)-5-[(2-β-epithiopropylselenoethyl)selenomethyl]-3,7-dithianonane, 1,10-bis(β-epithiopropylseleno)-5,6-bis[(2-β-epithiopropylselenoethyl)thio]-3,6,9-trithiadecane, 1,11-bis(β-epithiopropylseleno)-4,8-bis(β-epithiopropylselenomethyl)-3,6,9-trithiaundecane, 1,11-bis(β-epithiopropylseleno)-5,7-bis(β-epithiopropylselenomethyl)-3,6,9-trithiaundecane, 1,11-bis(β-epithiopropylseleno)-5,7-[(2-β- epithiopropylselenoethyl)selenomethyl]-3,6,9-trithiaundecane, 1,11-bis(β-epithiopropylseleno)-4,7-bis(β-epithiopropylselenomethyl)-3,6,9-trithiaundecane, tetra[2-(β-epithiopropylseleno)acetylmethyl]methane, 1,1,1-tri [2-(β-epithiopropylseleno)acetylmethyl]propane, tetra[2-(β-epithiopropylselenomethyl)acetylmethyl]methane, 1,1,1-tri [2-(β-epithiopropylselenomethyl)acetylmethyl]propane, bis (5,6-epithio-3-selenohexyl)selenide, 2,3-bis(6,7-thioepoxy-1-selena-4-selenoheptyl)-1-(3,4-thioepoxy-1-selenobutyl) propane, 1,1,3,3-tetrakis(4,5-thioepoxy-2-selenopentyl)-2-selenapropane, bis(4,5-thioepoxy-2-selenopentyl)-3,6,9-triselenaundecane-1,11-bis(3,4-thioepoxy-1-selenobutyl), 1,4-bis(3,4-thioepoxy-1-selenobutyl)-2,3-bis(6,7-thioepoxy-1-selena-4-selenoheptyl)butane, tris(4,5-thioepoxy-2-selenopentyl)-3-selena-6-thiaoctane-1,8-bis(3,4-thioepoxy-1-selenobutyl), bis(5,6-epithio-3-selenohexyl)telluride, 2,3-bis(6,7-thioepoxy-1-tellura-4-selenoheptyl)-1-(3,4-thioepoxy-1-selenobutyl)propane, 1,1,3,3-tetrakis(4,5-thioepoxy-2-selenopentyl)-2-tellurapropane, bis(4,5-thioepoxy-2-selenopentyl)-3,6,9-tritelluraundecane-1,11-bis (3,4-thioepoxy-1-selenobutyl), 1,4-bis(3,4-thioepoxy-1-selenobutyl)-2,3-bis(6,7-thioepoxy-1-tellura-4-selenoheptyl)butane and tris(4,5-thiepoxy-2-selenopentyl)-3-tellura-6-thiaoctane-1,8-bis(3,4-thioepoxy-1-selenobutyl);

D-2: Compounds having alicyclic backbone 1,3- or 1,4-bis(β-epithiopropylseleno)cyclohexane, 1,3- or 1,4-bis(β-epithiopropylselenomethyl)cyclohexane, bis[4-(β-epithiopropylseleno)cyclohexyl]methane, 2,2-bis[4-(β-epithiopropylseleno)cyclohexyl]propane, bis[4-(β-epithiopropylseleno)cyclohexyl] sulfide, 2,5-bis(β-epithiopropylselenomethyl)-1,4-dithiane, 2,5-bis(β-epithiopropylselenoethylthiomethyl)-1,4-dithiane, 2,3-, 2,5- or 2,6-bis(3,4-epithio-1-selenobutyl)-1,4-diselenane, 2,3-, 2,5- or 2,6-bis(4,5-epithio-2-selenopentyl)-1,4-diselenane, 2,4-, 2,5- or 5,6-bis(3,4-epithio-1-selenobutyl)-1,3-diselenane, 2,4-, 2,5- or 5,6-bis(4,5-epithio-2-selenopentyl)-1,3-diselenane, 2,3-, 2,5-, 2,6- or 3,5-bis(3,4-epithio-1-selenobutyl)-1-thia-4-selenane, 2,3-, 2,5-, 2,6- or 3,5-bis(4,5-epithio-2-selenopentyl)-1-thia-4-selenane, 2,4- or 4,5-bis(3,4-epithio-1-selenobutyl)-1,3-diselenolane, 2,4- or 4,5-bis(4,5-epithio-2-selenopentyl)-1,3-diselenolane, 2,4-, 2,5- or 4,5-bis(3,4-epithio-1-selenobutyl)-1-thia-3-selenolane, 2,4-, 2,5- or 4,5-bis(4,5-epithio-2-selenopentyl)-1-thia-3-selenolane, 2,6-bis(4,5-epitbio-2-selenopentyl)-1,3,5-triselenane, bis(3,4-epithio-1-selenobutyl)tricycloselenaoctane, bis(3,4-epithio-1-selenobutyl)dicycloselenanonane, 2,3-, 2,4-, 2,5- or 3,4-bis(3,4-epitbio-1-selenobutyl)selenophane, 2,3-, 2,4-, 2,5-, 3,4-bis(4,5-epithio-2-selenopentyl)selenophane, 2-(4,5-thioepoxy-2-selenopentyl)-5-(3,4-thioepoxy-1-selenobutyl)-1-selenacyclohexane, 2,3-, 2,4-, 2,5-, 2,6-, 3,4-, 3,5- or 4,5-bis(3,4-thioepoxy-1-selenobutyl)-1-selena 2,3-, 2,4-, 2,5-, 2,6-, 3,4-, 3,5- or 4,5-bis(4,5-thioepoxy-2-selenopentyl)-1-selen 2,3-, 2,5- or 2,6-bis(3,4-epithio-1-selenobutyl)-1,4-ditellurane, 2,3-, 2,5- or 2,6-bis(4,5-epithio-2-selenopentyl)-1,4-ditellurane, 2,4-, 2,5- or 5,6-bis(3,4-epithio-1-selenobutyl)-1,3-ditellurane, 2,4-, 2,5- or 5,6-bis(4,5-epithio-2-selenopentyl)-1,3-ditellurane, 2,3-, 2,5-, 2,6- or 3,5-bis(3,4-epithio-1-selenobutyl)-1-thia-4-tellurane, 2,3-, 2,5-, 2,6- or 3,5-bis(4,5-epithio-2-selenopentyl)-1-thia-4-tellurane, 2,4- or 4,5-bis(3,4-epithio-1-selenobutyl)-1,3-ditellurolane, 2,4- or 4,5-bis(4,5-epitbio-2-selenopentyl)-1,3-ditellurolane, 2,4-, 2,5- or 4,5-bis(3,4-epithio-1-selenobutyl)-1-thia-3-tellurolane, 2,4-, 2,5- or 4,5-bis(4,5-epithio-2-selenopentyl)-1-thia-3-tellurolane, 2,6-bis(4,5-epithio-2-selenopentyl)-1,3,5-tritellurane, bis(3,4-epithio-1-selenobutyl)tricycloselluraoctane, bis(3,4-epithio-1-selenobutyl)dicycloselluranonane, 2,3-, 2,4-, 2,5- or 3,4-bis(3,4-epithio-1-selenobutyl)tellurophane, 2,3-, 2,4-, 2,5- or 3,4-bis(4,5-epithio-2-selenopentyl)tellurophane, 2-(4,5-thioepoxy-2-selenopentyl)-5-(3,4-thioepoxy-1-selenobutyl)-1-telluracyclohexane, 2,3-, 2,4-, 2,5-, 2,6-, 3,4-, 3,5- or 4,5-bis(3,4-thioepoxy-1-selenobutyl)-1-telluracyclohexane, and 2,3-, 2,4-, 2,5-, 2,6-, 3,4-, 3,5- or 4,5-bis(4,5-thioepoxy-2-selenopentyl)-1-telluracyclohexane;

D-3: Compounds having aromatic backbone 1,3- or 1,4-bis(β-epithiopropylseleno)benzene, 1,3- or 1,4-bis(β-epithiopropylselenomethyl)benzene, bis[4-(β-epithiopropylseleno)phenyl]methane, 2,2-bis[4-(β-epithiopropylseleno)phenyl]propane, bis[4-(β-epithiopropylseleno)phenyl] sulfide, bis[4-(β-epithiopropylseleno)phenyl] sulfone and 4,4'-bis(β-epithiopropylseleno)biphenyl; and D-4: Compounds obtained by replacing at least one hydrogen of the β-epithiopropyl group in the compounds D-1 to D-3 with methyl.

Preferred examples of the compounds E (Y═Te) are epoxy compounds with one or more epoxyalkyltelluro groups (specifically, β-epoxypropyltelluro group) replaced by epithioalkyltelluro groups, the epoxy compounds being derived from an epihalohydrin and a tellurium compound such as mettalic tellurium, alkali metal tellurides, alkali metal tellurols, alkyl tellurols, aryl tellurols and hydrogen telluride. Specific examples are recited below.

E-1: Compounds having aliphatic chain backbone bis(β-epithiopropyl)telluride, bis(β-epidithiopropyl)telluride, bis(β-epithiopropyl)ditelluride, bis(β-epidithiopropyl)ditelluride, bis(β-epithiopropyl)tritelluride, bis(β-epithiopropyltelluro)methane, 1,2-bis(β-epithiopropyltelluro)ethane, 1,3-bis(β-epithiopropyltelluro)propane, 1,2-bis(β-epithiopropyltelluro)propane, bis(epithioethyl)telluride, bis(epithioethyl) ditelluride, 1-(β-epithiopropyltelluro)-2-(β-epithlopropyltelluromethyl)propane, 1,2,3-tris(β-epithiopropyltelluro)propane, 1,4-bis(β-epithiopropyltelluro)butane, 1,3-bis(β-epithiopropyltelluro)butane, 1-(β-epithiopropyltelluro)-3-(β-epithiopropyltelluromethyl)butane, 1,5-bis(β-epithiopropyltelluro)pentane, 1-(β-epithiopropyltelluro)-4-(β-epithiopropyltelluromethyl)pentane, 1,5-bis(β-epithlopropyltelluro)-2-β-epithiopropyltelluromethyl)-3-thiapentane, 1,6-bis(β-epithiopropyltelluro)hexane, 1-(β-epithiopropyltelluro)-5-(β-epithiopropyltelluromethyl) hexane, 1-(β-epithiopropyltelluro)-2-[(2-β-epithiopropyltelluroethyl)thio]ethane, 1-(β-epithiopropyltelluro)-2-[[2-(2-β-epithiopropyltelluroethyl)telluroethyl]thio]ethane, tetrakis(β-epithiopropyltelluromethyl)methane, 1,1,1-tris(β-epithiopropyltelluromethyl)propane, 1,5-bis(β-epithiopropyltelluro)-2-(β-epithiopropyltelluromethyl)-3-thiapentane, 1,5-bis(β-epithiopropyltelluro)-2,4-bis(β-epithiopropyltelluromethyl)-3-thiapentane, 1-(β-epithiopropyltelluro)-2,2-bis(β-epithiopropyltelluromethyl)-4-thiahexane, 1,5,6-tris(β-epithiopropyltelluro)-4-(β-epithiopropyltelluromethyl)-3-thiahexane, 1,8-bis(β-epithlopropyltelluro)-4-(β-epithiopropyltelluromethyl)-3,6-dithiaoctane, 1,8-bis(β-epithiopropyltelluro)-4,5-bis(β-epithiopropyltelluromethyl)-3,6-dithiaoctane, 1,8-bis(β-epithiopropyltelluro)-4,4-bis(β-epithiopropyltelluromethyl)-3,6-dithiaoctane, 1,8-bis(β-epithiopropyltelluro)-2,4,5-tris(β-epithiopropyltelluromethyl)-3,6-dithiaoctane, 1,8-bis(β-epithiopropyltelluro)-2,5-bis(β-epithiopropyltelluromethyl)-3,6-dithiaoctane, 1,9-bis(β-epithiopropyltelluro)-5-(β-epithiopropyltelluromethyl)-5-

[(2-β-epithiopropyltelluroethyl)selenomethyl]-3,7-dithianonane, 1,10-bis(β-epithiopropyltelluro)-5,6-bis[(2-β-epithiopropyltelluroethyl)thio]-3,6,9-trithiadecane, 1,11-bis(β-epithiopropyltelluro)-4,8-bis(β-epithiopropyltelluromethyl)-3,6,9-trithiaundecane, 1,11-bis(β-epithiopropyltelluro)-5,7-bis(β-epithiopropyltelluromethyl)-3,6,9-trithiaundecane, 1,11-bis(β-epithiopropyltelluro)-5,7-[(2-β-epithiopropyltelluroethyl)selenomethyl]-3,6,9-trithiaundecane, 1,11-bis(β-epithiopropyltelluro)-4,7-bis(β-epithiopropyltelluromethyl)-3,6,9-trithiaundecane, tetra[2-(β-epithiopropyltelluro)acetylmethyl]methane, 1,1,1-tri[2-(β-epithiopropyltelluro)acetylmethyl]propane, tetra[2-(β-epithiopropyltelluromethyl)acetylmethyl]methane, 1,1,1-tri[2-(β-epithiopropyltelluromethyl)acetylmethyl]propane, bis(5,6-epithio-3-tellurohexyl)selenide, 2,3-bis(6,7-thioepoxy-1-selena-4-telluroheptyl)-1-(3,4-thioepoxy-1-tellurobutyl)propane, 1,1,3,3-tetrakis(4,5-thioepoxy-2-telluropentyl)-2-selenapropane, bis(4,5-thioepoxy-2-telluropentyl)-3,6,9-triselenaundecane-1,11-bis(3,4-thioepoxy-1-tellurobutyl), 1,4-bis(3,4-thioepoxy-1-tellurobutyl)-2,3-bis(6,7-thioepoxy-1-selena-4-telluroheptyl)butane, tris(4,5-thioepoxy-2-telluropentyl)-3-selena-6-thiaoctane-1,8-bis(3,4-thioepoxy-1-tellurobutyl), bis(5,6-epithio-3-tellurohexyl)telluride, 2,3-bis(6,7-thioepoxy-1-tellura-4-telluroheptyl)-1-(3,4-thioepoxy-1-tellurohexyl)propane, 1,1,3,3-tetrakis(4,5-thioepoxy-2-telluropentyl)-2-tellurapropane, bis(4,5-thioepoxy-2-telluropentyl)-3,6,9-tritelleraundecane-1,11-bis(3,4-thioepoxy-1-tellurobutyl), 1,4-bis(3,4-thioepoxy-1-tellurobutyl)-2,3-bis(6,7-thioepoxy-1-tellura-4-telluroheptyl)butane and tris(4,5-thiepoxy-2-telluropentyl)-3-tellura-6-thiaoctane-1,8-bis(3,4-thioepoxy-1-tellurobutyl);

E-2: Compounds having alicyclic backbone 1,3- or 1,4-bis(β-epithiopropyltelluro)cyclohexane, 1,3- or 1,4-bis(β-epithiopropyltelluromethyl)cyclohexane, bis[4-(β-epithiopropyltelluro)cyclohexyl]methane, 2,2-bis[4-(β-epithiopropyltelluro)cyclohexyl]propane, bis[4-(β-epithiopropyltelluro)cyclohexyl]sulfide, 2,5-bis(β-epithiopropyltelluromethyl)-1,4-dithiane, 2,5-bis(β-epithiopropyltelluroethylthiomethyl)-1,4-dithiane, 2,3-, 2,5- or 2,6-bis(3,4-epithio-1-tellurobutyl)-1,4-diselenane, 2,3-, 2,5- or 2,6-bis(4,5-epithio-2-telluropentyl)-1,4-diselenane, 2,4-, 2,5- or 5,6-bis(3,4-epithio-1-tellurobutyl)-1,3-diselenane, 2,4-, 2,5- or 5,6-bis(4,5-epithio-2-telluropentyl)-1,3-diselenane, 2,3-, 2,5-, 2,6- or 3,5-bis(3,4-epithio-1-tellurobutyl)-1-thia-4-selenane, 2,3-, 2,5-, 2,6- or 3,5-bis(4,5-epithio-2-telluropentyl)-1-thia-4-selenolane, 2,4- or 4,5-bis(3,4-epithio-1-tellurobutyl)-1,3-diselenolane, 2,4- or 4,5-bis(4,5-epithio-2-telluropentyl)-1,3-diselenolane, 2,4-, 2,5- or 4,5-bis(3,4-epithio-1-tellurobutyl)-1-thia-3-selenoolane, 2,4-, 2,5- or 4,5-bis(4,5-epithio-2-telluropentyl)-1-thia-3-selenolane, 2,6-bis(4,5-epithio-2-telluropentyl)-1,3,5-triselenane, bis(3,4-epithio-1-tellurobutyl)tricycloselenaoctane, bis(3,4-epithio-1-tellurobutyl)dicycloselenanonane, 2,3-, 2,4-, 2,5- or 3,4-bis(3,4-epithio-1-tellurobutyl)selenophane, 2,3-, 2,4-, 2,5- or 3,4-bis(4,5-epithio-2-telluropentyl)selenophane, 2-(4,5-thioepoxy-2-telluropentyl)-5-(3,4-thioepoxy-1-tellurobutyl)-1-selenacyclohexane, 2,3-, 2,4-, 2,5-, 2,6-, 3,4-, 3,5- or 4,5-bis(3,4-thioepoxy-1-tellurobutyl)-1-selenacyclohexane, 2,3-, 2,4-, 2,5-, 2,6-, 3,4-, 3,5- or 4,5-bis(4,5-thioepoxy-2-telluropentyl)-1-selenacyclohexane, 2,3-, 2,5- or 2,6-bis(3,4-epithio-1-tellurobutyl)-1,4-ditellurane, 2,3-, 2,5- or 2,6-bis(4,5-epithio-2-telluropentyl)-1,4-ditellurane, 2,4-, 2,5- or 5,6-bis(3,4-epithio-1-tellurobutyl)-1,3-ditellurane, 2,4-, 2,5- or 5,6-bis(4,5-epithio-2-telluropentyl)-1,3-ditellurane, 2,3-, 2,5-, 2,6- or 3,5-bis(3,4-epithio-1-tellurobutyl)-1-thia-4-tellurane, 2,3-, 2,5-,2,6- or 3,5-bis(4,5-epithio-2-telluropentyl)-1-thia-4-tellurane, 2,4- or 4,5-bis(3,4-epithio-1-tellurobutyl)-1,3-ditellurolane, 2,4- or 4,5-bis(4,5-epithio-2-telluropentyl)-1,3-ditellurolane, 2,4-, 2,5- or 4,5-bis(3,4-epithio-1-tellurobutyl)-1-thia-3-tellurolane, 2,4-, 2,5- or 4,5-bis(4,5-epithio-2-telluropentyl)-1-thia-3-tellurolane, 2,6-bis(4,5-epithio-2-telluropentyl)-1,3,5-tritellurane, bis(3,4-epithio-1-tellurobutyl)tricyclotelluraocta bis(3,4-epithio-1-tellurobutyl)dicyclotelluranonane, 2,3-, 2,4-, 2,5- or 3,4-bis(3,4-epithio-1-tellurobutyl)tellurophane, 2,3-, 2,4-, 2,5- or 3,4-bis(4,5-epithio-2-telluropentyl)tellurophane, 2-(4,5-thioepoxy-2-telluropentyl)-5-(3,4-thioepoxy-1-tellurobutyl)-1-telluracyclohexane, 2,3-, 2,4-, 2,5-, 2,6-, 3,4-, 3,5- or 4,5-bis(3,4-thioepoxy-1-tellurobutyl)-1-telluracyclohexan 2,3-, 2,4-, 2,5-, 2,6-, 3,4-, 3,5- or 4,5-bis(4,5-thioepoxy-2-telluropentyl)-1-tell E-3: Compounds having aromatic backbone 1,3- or 1,4-bis(β-epithiopropyltelluro)benzene, 1,3- or 1,4-bis(β-epithiopropyltelluromethyl)benzene, bis[4-(β-epithiopropyltelluro)phenyl]methane, 2,2-bis[4-(β-epithiopropyltelluro)phenyl]propane, bis[4-(β-epithiopropyltelluro)phenyl]sulfide, bis[4- (β-epithiopropyltelluro)phenyl]sulfone, and 4,4'-bis(β-epithiopropyltelluro)biphenyl; and E-4: Compounds obtained by replacing at least one hydrogen of the β-epithiopropyl group in the compounds E-1 to E-3 with methyl.

The episulfide compounds A to E may have an unsaturated group. Examples of such compounds include vinylphenyl thioglycidyl ether, vinylbenzyl thioglycidyl ether, thioglycidyl methacrylate, thioglycidyl acrylate and allyl thioglycidyl ether.

The episulfide compounds are not limited to those mentioned above and may be used alone or in combination of two or more.

Of the above compounds, preferred are the compounds B (Y=O), the compounds C (Y=S), and the compounds D (Y=Se), and more preferred are the compounds C and D. Still more preferred are the compounds C and D wherein m is 1 or 2, and n is 1 or 2, and the most preferred are the compounds C and D wherein $R^1$ is a single bond or methylene, m is 1, and n is 1 or 2. Examples of the most preferred compounds include bis(β-epithiopropyl)sulfide, bis(β-epithioethyl)sulfide, bis(β-epithiopropyl)selenide, bis(β-epithioethyl)selenide, and compounds having two or more β-epithiopropylthio groups, β-epithioethylthio groups, β-epithiopropylseleno groups or β-epithioethylseleno groups together with the aliphatic chain backbone, the aliphatic branched backbone, the alicyclic backbone, the aromatic backbone or the heterocyclic backbone mentioned above. Especially preferred of the above are chain or branched compounds having two or more β-epithiopropylthio groups, β-epithioethylthio groups, β-epithiopropylseleno groups or β-epithioethylseleno groups; bis(β-epithiopropyl)sulfide; bis(β-epithioethyl)sulfide; bis(β-epithiopropyl)selenide; and bis(β-epithioethyl)selenide.

In the present invention, the episulfide compound is polymerized under heating into a cured resin in the presence of the polymerization regulator and/or the halogen-containing stabilizer, and in the presence or absence, preferably in the presence of a curing catalyst. As the curing catalyst, amines, quaternary ammonium salts, phosphines, quaternary phosphonium salts, tertiary sulfonium salts, secondary iodonium salts, mineral acids, Lewis acids, organic acids, tin compounds, silicic acids and tetrafluoroboric acid, each listed below, are used.

Amines:

Primary amines such as ethylamine, n-propylamine, sec-propylamine, n-butylamine, sec-butylamine, isobutylamine, tert-butylamine, pentylamine, hexylamine, heptylamine, octylamine, decylamine, laurylamine, myristylamine, 1,2-dimethylliexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxy)propylamine, aminocyclopentane, aminocycilohexane, aminonorbornene, aminomethylcyclohexane, aminobenzene, benzylamine, phenetylamine, α-phenylethylamine, naphthylamine and furfurylamine; primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl)ether, 1,2-bis-(3-aminopropoxy)ethane, 1,3-bis-(3-aminopropoxy)-2,2'-dimethylpropane, aminoethylethanolamine, 1,2-, 1,3- or 1,4-bisaminocyclohexane, 1,3- or 1,4-bisaminomethylcyclohexane, 1,3- or 1,4-bisaminoethylcyclohexane, 1,3- or 1,4-bisaminopropylcyclohexane, hydrogenated 4,4'-diaminodiphenylmethane, 2- or 4-aminopiperidine, 2- or 4-aminomethylpiperidine, 2- or 4-aminoethylpiperidine, N-aminoethylpiperidine, N-aminopropylpiperidine, N-aminoethylmorpholine, N-aminopropylmorpholine, isophoronediamine, menthanediamine, 1,4-bisaminopropylpiperadine, o-, m- or p-phenylenediamine, 2,4- or 2,6-tolylenediamine, 2,4-toluene diamine, m-aminobenzylamine, 4-chloro-o-phenylenediamine, tetrachloro-p-xylylenediamine, 4-methoxy-6-methyl-m-phenylenediamine, m- or p-xylylenediamine, 1,5- or 2,6-naphthalenediamine, benzidine, 4,4'-bis(o-toluidine), dianisidine, 4,4'-diaminodiphenylmethane, 2,2-(4,4'-diaminodiphenyl)propane, 4,4'-diaminodiphenyl ether, 4,4'-thiodianiline, 4,4'-diaminodiphenyl sulfone, 4,4'-diaminoditolyl sulfone, methylenebis(o-chioroaniline), 3,9-bis(3-aminopropyl)-2,4,8,10-tetraoxaspiro[5.5]undecane, diethylenetriamine, iminobispropylamine, methyliminobispropylamine, bis(hexamethylene)triamine, triethylenetetramine, tetraethylenepentamine, pentaethylenehexamine, N-aminoethylpiperadine, N-aminopropylpiperadine, 1,4-bis(aminoethylpiperadine), 1,4-bis(aminopropylpiperadine), 2,6-diaminopyridine and bis(3,4-diaminophenyl)sulfone; secondary amines such as diethylamine, dipropylamine, di-n-butylamine, di-sec-butylamine, diisobutylamine, di-n-pentylamine, di-3-pentylamine, dihexylamine, dioctylamine, di(2-ethylhexyl)amine, methyihexylamine, diallylamine, pyrrolidine, piperidine, 2-, 3- or 4-picoline, 2,4-, 2,6- or 3,5-lupetidine, diphenylamine, N-methylaniline, N-ethylaniline, dibenzylamine, methylbenzylamine, dinaphthylamine, pyrrol, indoline, indole and morpholine; secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- or 2,6-dimethylpiperadine, homopiperadine, 1,1-di(4-piperidyl)methane, 1,2-di(4-piperidyl)ethane, 1,3-di(4-piperidyl)propane, 1,4-di(4-piperidyl)butane and tetramethylguanidine; tertiary amines such as trimethylamine, triethylamine, tri-n-propylamine, triisopropylamine, tri(1,2-dimethylpropyl)amine, tri(3-methoxypropyl)amine, tri-n-butylamine, triisobutylamine, tri-sec-butylamine, tri-n-pentylamine, tri-3-pentylamine, tri-n-hexylamine, tri-n-octylamine, tri(2-ethylhexyl)amine, tri-dodecylamine, trilaurylamine, dicyclohexylethylamine, cyclohexyldiethylamine, tricyclohexylamine, N,N-dimethylhexylamine, N-methyldihexylamine, N,N-dimethylcyclohexylamine, N,N-diethylcyclohexylamine, N-methyldicyclohexylamine, N,N-diethylethanolamine, N,N-dimethylethanolamine, N-ethyldiethanolamine, triethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenOl, N,N-dimethylaniline, N,N-diethylaniline, pyridine, quinoline, N-methylmorpholine, N-methylpiperidine and 2-(2-dimethylaminoethoxy)-4-methyl-1,3,2-dioxabornane; tertiary polyamines such as tetramethylethylenediamine, pyrazine, N,N'-dimethylpiperadine, N,N'-bis(2-hydroxypropyl)piperadine, hexamethylenetetramine, N,N,N',N'-tetramethyl-1,3-butaneamine, 2-dimethylamino-2-hydroxypropane, diethyaminoethanol, N,N,N-tris(3-dimethylaminopropyl)amine, 2,4,6-tris(N,N,-dimethylaminomethyl)phenol and heptamethylisobiguanide; imidazoles such as imidazole, N-methylimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 2-mercaptoimidazole, 2-mercapto-N-methylimidazole, 2-mercaptobenzimidazole, 3-mercapto-4-methyl-4H-1,2,4-triazole, 5-mercapto-1-methyl-tetrazole, 2,5-dimercapto-1,3,4-thiadiazole, 1-benzyl-2-methylimidazole, N-(2'-cyanoethyl)-2-methylimidazole, N-(2'cycanoethyl)-2-undecylimidazole, N-(2'-cyanoethyl)-2-phenylimidazole, 3,3-bis-(2-ethyl-4-methylimidazolyl)methane, addition products of alkylimidazoles and isocyanuric acid and condensation products of alkylimidazoles and formaldehyde; and amidines such as 1,8-diazabicyclo[5.4.0]undecene-7,1,5-diazabicyclo[4.3.0]nonene-5, 6-dibutylamino-1,8-diazabicyclo[5.4.0]undecene-7. The amine compounds may be used as the curing catalyst in the form of a complex with borane or boron trifluoride;

Quaternary Ammonium Salts:

Tetramethylammonium chloride, tetramethylammonium bromide, tetramethylammonium acetate, tetraethylammonium chloride, tetraethylammonium bromide, tetraethylammonium acetate, tetra-n-butylammonium fluoride, tetra-n-butylammonium chloride, tetra-n-butylammonium bromide, tetra-n-butylammonium iodide, tetra-n-butylammonium acetate, tetra-n-butylammonium borohydride, tetra-n-butylammonium hexafluorophosphite, tetra-n-butylammonium hydrogensulfite, tetra-n-butylammonium tetrafluoroborate, tetra-n-butylammonium tetraphenylborate, tetra-n-butylammonium p-toluenesulfonate, tetra-n-hexylammonium chloride, tetra-n-hexylammonium bromide, tetra-n-hexylammonium acetate, tetra-n-octylammonium chloride, tetra-n-octylammonium bromide, tetra-n-octylammonium acetate, trimethyl-n-octylammonium chloride, trimethylbenzylammonium chloride, trimethylbenzylammonium bromide, triethyl-n-octylammonium chloride, triethylbenzylammonium chloride, triethylbenzylammonium bromide, tri-n-butyl-n-octylammonium chloride, tri-n-butylbenzylammonium fluoride, tri-n-butylbenzylammonium chloride, tri-n-butylbenzylammonium bromide, tri-n-butylbenzylammonium iodide, methyltriphenylammonium chloride, methyltriphenylammonium bromide, ethyltriphenylammonium chloride, ethyltriphenylammonium bromide, n-butyltniphenylammonium chloride, n-butyltriphenylammonium bromide, 1-methylpyridinium bromide, 1-ethylpynidinium bromide, 1-n-butylpyridinium bromide, 1-n-hexylpyridinium bromide, 1-n-octylpynidinium bromide, 1-n-dodecylpyridinium bromide, 1-phenylpyridinium bromide, 1-methylpicolinium bromide, 1-ethylpicolinium bromide, 1-n-butylpicolinium bromide, 1-n-hexylpicolinium bromide, 1-n-octylpicolinium bromide, 1-n-dodecylpicolinium bromide and 1-phenylpicolinium bromide;

Phosphines:

Trimethyiphosphine, triethyiphosphine, triisopropylphosphine, tri-n-butylphosphine, tri-n-hexylphosphine, tni-n-octylphosphine, tricyclohexyiphosphine, triphenyiphosphine, tribenzylphosphine, tris(2-methylphenyl)phosphine, tris(3-methylphenyl)phosphine, tris(4-methylphenyl)phosphine, tris(diethylamino)phosphine, tris(4-methylphenyl)phosphine, dimethylphenylphosphine, diethylphenylphosphine, dicyclohexylphenylphosphine, ethyldiphenylphosphine, diphenylcyclohexylphosphine and chlorodiphenylphosphine;

Quaternary Phosphonium Salts:

Tetramethylphosphonium chloride, tetramethylphosphonium bromide, tetraethylphosphonium chloride, tetraethylphosphonium bromide, tetra-n-butylphosphonium chloride, tetra-n-butylphosphonium bromide, tetra-n-butylphosphonium iodide, tetra-n-hexylphosphonium bromide, tetra-n-octylphosphonium bromide, methyltriphenylphosphonium bromide, methyltriphenylphosphonium iodide, ethyltriphenylphosphonium bromide, ethyltriphenylphosphonium iodide, n-butyltriphenylphosphonium bromide, n-butyltriphenylphosphonium iodide, n-hexyltriphenylphosphonium bromide, n-octyltriphenylphosphonium bromide, tetraphenylphosphonium bromide, tetrakishydroxymethylphosphonium chloride, tetrakishydroxymethylphosphonium bromide, tetrakishydroxyethylphosphoniUm chloride and tetrakishydroxybutylphosphoniUm chloride;

Sulfonium Salts:

Trimethylsulfonium bromide, triethylsulfonium bromide, tn-n-butylsulfonium chloride, tri-n-butylsulfonium bromide, tri-n-butylsulfonium iodide, tri-n-butylsulfonium tetrafluoroborate, tri-n-hexylsulfonium bromide, tri-n-octylsulfonium bromide, triphenylsulfonium chloride, triphenylsulfonium bromide and triphenylsulfonium iodide;

Secondary Iodonium Salts:

Diphenyliodonium chloride, diphenyliodonium bromide and diphenyliodonium iodide;

Mineral Acids:

Hydrochloric acid, sulfuric acid, nitric acid, phosphoric acid and carbonic acid, and half-esters of these mineral acids;

Lewis Acids:

Boron trifluoride and boron trifluoride etherates;

Organic Acids:

Several organic acids and half-esters thereof and

Tin Compounds:

Dibutyltin dilaurate and dibutyltin diacetate.

The curing catalyst is not limited to the compounds listed above as far as it effectively polymerizes the episulfide compound in the presence of the polymerization regulator and/or the halogen-containing stabilizer. Among the above compounds, primary monoamines, secondary monoamines, tertiary monoamines, tertiary polyamines, imidazoles, amidines, quaternary ammonium salts, phosphines, quaternary phosphonium salts, tertiary sulfonium salts, and secondary iodonium salts are preferable because these compounds cause little coloring of the cured products. More preferred catalysts are quaternary ammonium salts, quaternary phosphonium salts, tertiary sulfonium salts, and secondary iodonium salts, and most preferred catalysts are quaternary ammonium salts and quaternary phosphonium salts. These compounds may be used singly or in combination of two or more.

Although the amount of the curing catalyst to be used varies depending on the type and the addition amount of the polymerization regulator and the halogen-containing stabilizer, and not strictly limited, the amount is generally 0.001 to 5.0 parts by weight, preferably 0.005 to 3.0 parts by weight, more preferably 0.01 to 1.0 part by weight and most preferably 0.01 to 0.5 part by weight per 100 parts by weight of the episulfide compound. When the amount of the curing catalyst exceeds 5.0 parts by weight, the refractive index and heat resistance of the cured product decrease and the cured product is colored. When the amount is less than 0.001 part by weight, the curing does not proceed sufficiently and heat resistance becomes insufficient.

To enhance the impact resistance of the cured resin (optical material) of the present invention, a compound having, in one molecule, at least one isocyanate group and/or isothiocyanate group may be added as an impact resistance improver. Examples thereof include monoisocyanates such as methyl isocyanate, ethyl isocyanate, propyl isocyanate, isopropyl isocyanate, n-butyl isocyanate, sec-butyl isocyanate, tert-butyl isocyanate, pentyl isocyanate, hexyl isocyanate, octyl isocyanate, dodecyl isocyanate, cyclohexyl isocyanate, phenyl isocyanate and toluyl isocyanate; polyisocyanates such as diethylene diisocyanate, tetramethylene diisocyanate, hexamethylene diisocyanate, trimethylhexamethylene diisocyanate, cyclohexane diisocyanate, 1,3-bis(isocyanatomethyl)cyclohexane, 1,4-bis(isocyanatomethyl)cyclohexane, isophorone diisocyanate, 2,6-bis(isocyanatomethyl)decahydronaphthalene, lysine triisocyanate, 2,4-tolylenediisocyanate, 2,6-tolylene diisocyanate, o-tolydyne diisocyanate, 4,4'-diphneylmethane diisocyanate, diphenyl ether diisocyanate, 3-(2'-isocyanatecyclohexyl)propyl isocyanate, tris(phenylisocyanate)thiophosphate, isopropylidene bis(cyclohexylisocyanate), 2,2'-bis(4-isoisocyanatephenyl)propane, triphenylmethane triisocyanate, bis(diisocyanatetolyl)phenylmethane, 4,4',4"-triisocyanate-2,5-dimethoxyphenylamine, 3,3'-dimethoxybenzidine -4,4'-diisocyanate, 1,3-phenylene diisocyanate, 1,4-phenylene diisocyanate, 4,4'-diisocyanatobiphenyl, 4,4'-diisocyanato-3,3'-dimethylbiphenyl, dicyclohexylmethan-4,4'-diisocyanate, 1,1'-methylenebis(4-isocyanatobenzene), 1,1'-methylenebis(3-methyl-4-isocyanatobenzene), m-xylylene diisocyanate, p-xylylene diisocyanate, 1,3-bis(1-isocyanate-1-methylethyl)benzene, 1,4-bis(1-isocyanate-1-methylethyl)benzene, 1,3-bis(2-isocyanato-2-propyl)benzene, 2,6-bis(isocyanatomethyl)naphthalene, 1,5-naphthalene diisocyanate, bis(isocyanatemethyl)tetrahydrodicyclopentadiene, bis(isocyanatemethyl)dicyclopentadiene, bis(isocyanatemethyl)tetrahydrothiophene, bis(isocyanatemethyl)thiophene, 2,5-diisocyanatemethylnorbornene, bis(isocyanatemethyl)adamantane, 3,4-diisocyanateselenophane, 2,6-diisocyanate-9-selenabicyclononane, bis(isoisocyanatemethyl)selenophane, 3,4-diisocyanate-2,5-diselenorane, dimeric acid diisocyanate, 1,3,5-tri(1-isoisocyanatehexyl)isocyanuric acid, 2,5-diisocyanatomethyl-1,4-dithiane, 2,5-bis(4-isocyanato-2-thiabutyl)-1,4-dithiane, 2,5-bis(3-isocyanatomethyl-4-isocyanato-2-thiabutyl)-1,4-dithiane, 2,5-bis(3-isocyanato-2-thiapropyl)-1,4-dithiane, 1,3,5-triisocyanatocyclohexane, 1,3,5-tris(isocyanatomethyl)cyclohexane, bis(isocyanatomethylthio)methane, 1,5-diisocyanato-2-isocyanatomethyl-3-thiapentane, 1,2,3- tris(isocyanatoethylthio)propane, 1,2,3-tris(isocyanatomethylthio)propane, 1,1,6,6-tetrakis(isocyanatomethyl)-2,5-dithiahexane, 1,1,5,5-tetrakis(isocyanatomethyl) 2,4-dithiapentane, 1,2-bis(isocyanatomethylthio)ethane, 1,5- diisocyanato-3-isocyanatomethyl-2,4-dithiapentane, and 1,5diisocyanato-3-isocyanatomethyl-2,4-dithiapentane; dimers of the polyisocyanates obtained by the biuret reaction; cyclic trimers of the polyisocyanates; addition products of the polyisocyanates with alcohols or thiols; and compounds obtained by replacing entirely or partially the isocyanato groups of the above compound by isothiocyanate groups.

To enhance the oxidation resistance of the cured resin of the present invention, a phenol compound or a compound having at least one mercapto group may be used as an anti-oxidation improver solely or in combination with a known antioxidant. Examples of the phenol compounds include phenol, cresol, catechol, and resorcinol. Examples of the compound having at least one mercapto group include mercaptans and thiophenols, each optionally having an unsaturated group such as vinyl group, aromatic vinyl groups, methacryl group, acryl group and ally group.

Examples of the mercaptans include monomercaptans such as methyl mercaptan, ethyl mercaptan, n-propyl mercaptan, n-butyl mercaptan, allyl mercaptan, n-hexyl mercaptan, n-octyl mercaptan, n-decyl mercaptan, n-dodecyl mercaptan, n-tetradecyl mercaptan, n-hexadecyl mercaptan, n-octadecyl mercaptan, cyclohexyl mercaptan, isopropyl mercaptan, tert-butyl mercaptan, tert-nonyl mercaptan, tert-dodecyl mercaptan, benzyl mercaptan, 4-chlorobenzyl mercaptan, methyl thioglycolate, ethyl thioglycolate, n-butyl thioglycolate, n-octyl thioglycolate, methyl (3-mercaptopropionate), ethyl (3-mercaptopropionate), 3-methoxybutyl (3-mercaptopropionate), n-butyl (3-mercaptopropionate), 2-ethylhexyl (3-mercaptopropionate), n-octyl (3-mercaptopropionate), 2-mercaptoethanol, 3-mercaptoethanol, 2-mercaptopropanol, 2-hydroxypropylmercaptan, 2-phenyl-2-mercaptoethanol, 2-phenyl-2-hydroxyethylmercaptan, 3-mercapto-1,2-propanediol and 2-mercapto-1,3-propanediol; polymercaptans such as methanedithiol, 1,2-dimercaptoethane, 1,2-dimercaptopropane, 2,2-dimercaptopropane, 1,3-dimercaptopropane, 1,2,3-trimercaptopropane, 1,4-dimercaptobutane, 1,6-dimercaptohexane, bis(2-mercaptoethyl)sulfide, 1,2-bis(2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane -1,2-dithiol, 2-mercaptomethyl-1,3-dimercaptopropane, 2-mercaptomethyl-1,4-dimercaptobutane, 2- (2-mercaptoethylthio)-1,3-dimercaptopropane, 1,2-bis(2-mercaptoethylthio)-3-mercaptopropane, 1,1,1-tris(mercaptomethyl)propane, tetrakis(mercaptomethyl)methane, ethylene glycol bis(2-mercaptoacetate), ethylene glycol bis(3-mercaptopropionate), 1,4-butanediol bis(2-mercaptoacetate), 1,4-butanediol bis(3-mercaptopropionate), trimethylolpropane tris(2-mercaptoacetate), trimethyloipropane tris(3-mercaptopropionate), pentaerythritol tetrakis(2-mercaptoacetate), pentaerythritol tetrakis(3-mercaptopropionate), 1,1-dimercaptocyclohexane, 1,4-dimercaptocyclohexane, 1,3-dimercaptocyclohexane, 1,2-dimercaptocyclohexane, 1,4-bis(mercaptomethyl)cyclohexane, 1,3-bis-(mercaptomethyl)cyclohexane, 2,5-bis(mercaptomethyl)-1,4-dithiane, 2,5-bis(2-mercaptoethy)-1,4-dithiane, 2,5-bis(mercaptomethyl)-1-thiane, 2,5-bis(2-mercaptoethyl)-1-thiane, 1,4-bis(mercaptomethyl)benzene, 1,3-bis(mercaptomethyl)benzene, bis(4-mercaptophenyl)sulfide, bis(4-mercaptophenyl)ether, 2,2-bis(4-mercaptophenyl)propane, bis(4-mercaptomethylphenyl)sulfide, bis(4-mercaptomethylphenyl)ether, 2,2-bis(4-mercaptomethylphenyl)propane, 2,5-dimercapto-1,3,4-thiadiazole, 3,4-thiophenedithiol, 1,2-dimercapto-3-propanol, 1,3-dimercapto-2-propanol and glyceryl dithioglycolate; and oligomers of 2 to 20 monomeric polymercaptanes.

Examples of the thiophenols include thiophenol, 4-tert-butyithiophenol, 2-methylthiophenol, 3-methylthiophenol, 4-methylthiophenol, 1,2-dimercaptobenzene, 1,3-dimercaptobenzene, 1,4-dimercaptobenzene, 2-hydroxythiophenol, 3-hydroxythiophenol and 4-hydroxythiophenol.

Examples of the mercaptans having an unsaturated group include allyl mercaptan, 2-vinylbenzyl mercaptan, 3-vinylbenzyl mercaptan and 4-vinylbenzyl mercaptan.

Examples of the thiophenols having an unsaturated group include 2-vinylthiophenol, 3-vinylthiophenol and 4-vinylthiophenol.

To increase the refractive index of the cured resin, a refractive index improver may be added which is selected from sulfur, selenium and inorganic compounds having at least one sulfur atom and/or selenium atom. The total weight of sulfur atom and/or selenium atom in the inorganic compounds is preferably 30% or more. If less than 30%, the effect of increasing the refractive index of the cured resin is insufficient because the weight ratio of sulfur atom and/or selenium atom in the starting composition for the optical material does not increases so much.

Examples of the inorganic compound having sulfur atom include hydrogen sulfide, carbon disulfide, carbon selenosulfide, ammonium sulfide, oxides of sulfur such as sulfur dioxide and sulfur trioxide, salts of thiocarbonic acid, sulfuric acid, salts of sulfuric acid, salts of hydrogensulfuric acid, salts of sulfurous acid, salts of hyposulfurous acid, salts of persulfuric acid, salts of thiocyanic acid, salts of thiosulfuric acid, sulfur-containing halogen compounds such as sulfur dichloride, thionyl chloride and thiophosgen, boron sulfide, nitrogen sulfide, silicon sulfide, phosphorus sulfide, arsenic sulfide, selenium sulfide, metal sulfides and metal hydrogensulfides.

Examples of the inorganic compound having selenium atom include hydrogen selenide, selenium dioxide, carbon diselenide, ammonium selenide, oxides of selenium such as selenium dioxide, selenic acid, salts of selenic acid, selenous acid, salts of selenous acid, salts of hydrogenselenic acid, selenosulfuric acid, salts of selenosulfuric acid, selenopyrosulfuric acid, salts of selenopyrosulfuric acid, selenium-containing halides such as selenium tetrabromide and selenium oxychloride, salts of selenocyanic acid, boron selenide, phosphorus selenide, arsenic selenide and metal selenides.

To improve the dyeability, mechanical strength, etc. of the cured resin of the present invention, a compound having one or more active hydrogen atoms other than mercapto hydrogen may be used. The active hydrogen atom referred to herein is hydroxyl hydrogen, carboxyl hydrogen, amide hydrogen, and hydrogen at the 2-position of 1,3-diketones, 1,3-dicarboxylic acids, esters of 1,3-dicarboxylic acids, 3-ketocarboxylic acids, and esters of 3-ketocarboxylic acids.

Examples of the compound having at least one active hydrogen atom include alcohols, phenols, mercaptoalcohols, hydroxythiophenols, carboxylic acids, mercaptocarboxylic acids, hydroxycarboxylic acids, amides, 1,3-diketones, 1,3-dicarboxylic acids, esters of 1,3-dicarboxylic acids, 3-ketocarboxylic acids, esters of 3-ketocarboxylic acids, and compounds having an unsaturated group such as vinyl group, aromatic vinyl groups, methacrylic group, acrylic group and allyl group. The compound having an unsaturated group may include such as alcohols, phenols, mercaptans, mercaptoalcohols, (hydroxy)thiophenols, carboxylic acids, mercaptocarboxylic acids, hydroxycarboxylic acids, amides, 1,3-diketones, 1,3-dicarboxylic acids, esters of 1,3-dicarboxylic acids, 3-ketocarboxylic acids and esters of 3-ketocarboxylic acids.

Examples of the alcohols include monohydric alcohols such as methanol, ethanol, n-propyl alcohol, isopropyl alcohol, n-butyl alcohol, isobutyl alcohol, sec-butyl alcohol, tert-butyl alcohol, n-pentyl alcohol, isopentyl alcohol, n-hexyl alcohol, n-heptyl alcohol, n-octyl alcohol, n-nonyl alcohol, n-decyl alcohol, n-dodecyl alcohol, cyclopentanol, cyclohexanol, 2-methylthioethanol, 2-ethylthioethanol, 2-(n-dodecylthio)ethanol and n-dodecyl hydroxyethyl sulfoxide; and polyhydric alcohols such as ethylene glycol, propylene glycol, 1,3-propanediol, diethylene glycol, triethylene glycol, polyethylene glycol, 1,3-butylene glycol, 1,6-hexanediol, neopentyl glycol, polypropylene glycol, glycerol, pentaerythritol monomethacrylate, pentaerythritol monoacrylate, pentaerythritol dimethacrylate, pentaerythritol diacrylate, 2,5-dimethyl-3-hexyne-2,5-diol, 2,5-dimethylhexane-2,5-diol, trimethylolpropane, pentaerythritol, hydrogenated bisphenol A, 2-hydroxyethyl isocyanurate and 2-hydroxyethyl cyanurate.

Examples of the phenols include phenol, o-cresol, m-cresol, p-cresol, catechol, resorcinol, hydroquinone, o-hydroxybenzaldehyde, m-hydroxybenzaldehyde, p-hydroxybenzaldehyde, bisphenol A, bisphenol F and bisphenol Z.

Examples of the mercaptoalcohols include 2-mercaptoethanol, 3-mercaptopropanol, 2-mercaptopropanol, 2-hydroxypropylmercaptan, 2-phenyl-2-mercaptoethanol, 2-phenyl-2-hydroxyethylmercaptan, 3-mercapto-1,2-propanediol, 2-mercapto-1,3-propanediol, 2,3-dimercaptopropanol, 1,3-dimercapto-2-propanol, 2,2-dimethyipropane-1,3-dithiol and glyceryl dithioglycolate.

Examples of the hydroxythiophenols include 2-hydroxythiophenol, 3-hydroxythiophenol and 4-hydroxythiophenol.

Examples of the carboxylic acids include formic acid, acetic acid, propionic acid, butyric acid, valeric acid, caproic acid, caprylic acid, methyl mercaptopropionate, oxalic acid, malonic acid, succinic acid, glutaric acid, adipic acid, cyclohexanecarboxylic acid, benzoic acid, o-toluic acid, m-toluic acid, p-toluic acid, 2-methoxybenzoic acid, 3-methoxybenzoic acid, phthalic acid, isophthalic acid, terephthalic acid, thiodipropionic acid and dithiodipropionic acid.

Examples of the mercaptocarboxylic acids include thioglycolic acid, 2-thiopropionic acid, 3-thiopropionic acid, thiolactic acid, mercaptosuccinic acid, thiomalic acid, N-(2-mercaptopropionyl)glycine, 2-mercaptobenzoic acid, 2-mercaptonicotinic acid, 3,3-dithioisobutyric acid, dithioglycolic acid, and dithiopropionic acid.

Examples of the hydroxycarboxylic acids include hydroxyacetic acid, α-hydroxypropionic acid, β-hydroxypropionic acid, α-hydroxybutyric acid, β-hydroxybutyric acid, γ-hydroxybutyric acid, salicylic acid, 3-hydroxybenzoic acid and 4-hydroxybenzoic acid.

Examples of the amides include formamide, N-methylformamide, acetamide, N-methylacetamide, phthalamide, isophthalamide, terephthalamide, benzamide, toluamide, 4-hydroxybenzamide and 3-hydroxybenzamide.

Examples of the 1,3-diketones include acetylacetone and cyclohexane-1,3,5-trione.

Examples of the 1,3-dicarboxylic acids and the ester thereof include malonic acid, 2-methylmalonic acid and mono- and diesters thereof.

Examples of the 3-ketocarboxylic acids and the ester thereof include acetoacetic acid and esters thereof.

Examples of the alcohols, phenols, mercaptans, thiophenols, mercaptoalcohols, carboxylic acids and amides each having an unsaturated group are as follows.

Examples of the alcohols having an unsaturated group include monohydroxy compounds such as 2-hydroxyethyl methacrylate, 2-hydroxyethyl acrylate, 3-hydroxypropyl methacrylate, 3-hydroxypropyl acrylate, 2-hydroxypropyl methacrylate, 2-hydroxypropyl acrylate, 1,3- dimethacryloxy-2-propanol, 1,3- diacryloxy-2-propanol, 1-acryloxy-3-methacryloxy-2-propanol, pentaerythritol trimethacrylate, pentaerythritol triacrylate, bis(2,2,2-trimethylolethyl)ether pentamethacrylate, bis(2,2,2-trimethylolethyl)ether pentaacrylate, trimethylolpropane dimethacrylate, trimethylolpropane diacrylate, allyl alcohol, crotyl alcohol, methyl vinyl carbinol, cinnamyl alcohol, 4-vinylbenzyl alcohol, 3-vinylbenzyl alcohol, 2-(4-vinylbenzylthio)ethanol, 2-(3-vinylbenzylthio)ethanol, 1,3-bis(4-vinylbenzylthio)-2-propanol, 1,3-bis(3-vinylbenzylthio)-2-propanol, 2,3-bis(4-vinylbenzylthio)-1-propanol, 2,3-bis(3-vinylbenzylthio)-1-propanol, 3-phenoxy-2-hydroxylpropyl acrylate, 2-hydroxyethyl isocyanurate bis(acrylate), 2-hydroxyethyl isocyanurate bis(methacrylate), 2-hydroxyethyl cyanurate bis(acrylate), 2-hydroxyethyl cyanurate bis(methacrylate), 3-methyl-1-butyn-3-ol, 3-methyl-1-pentyn-3-ol and propargyl alcohol; polyhydroxy compounds such as pentaerythritol dimethacrylate, pentaerythritol diacrylate, pentaerythritol monomethacrylate, pentaerythritol monoacrylate, trimethylolpropane monomethacrylate, trimethylolpropane monoacrylate, 2-hydroxyethyl isocyanurate monoacrylate, 2-hydroxyethyl isocyanurate monomethacrylate, 2-hydroxyethyl cyanurate monoacrylate and 2-hydroxyethyl cyanurate monomethacrylate; and unsaturated polyhydroxy compounds, such as 2,2-bis[4-(2-hydroxy-3-methacryloxypropoxy)pheflyl]propane, formed by the addition reaction of acrylic acid or methacrylic acid with an epoxy compound that is described later.

Examples of the phenols having an unsaturated group include 2-vinyiphenol, 3-vinylphenol and 4-vinylphenol.

Examples of the mercaptoalcohols having an unsaturated group include 2-(4-vinylbenzylthio)-2-mercaptoethanol and 2-(3-vinylbenzylthio)-2-mercaptoethanol.

Examples of the carboxylic acids having an unsaturated group include acrylic acid, methacrylic acid, crotonic acid, monohydroxyethyl acrylate phthalate, maleic acid, fumaric acid, monoallyl phthalate and cinnamic acid.

Examples of the amides having an unsaturated group include amides of α,β-unsaturated carboxylic acids such as acrylic acid, methacrylic acid, maleic acid, maleic anhydride and fumaric acid; and N-vinylformamide.

These compounds may be used alone or in combination of two or more in an amount of 0.001 to 40 parts by weight based on 100 parts by weight of the episulfide compound.

In addition to the dyeability-improving compound mentioned above, the resin of the present invention may be produced by curing the composition for optical material together with a compound having two or more functional groups reactive with the epithio structure of Formula 2; a compound having one or more functional groups reactive with the epithio structure and one or more other homopolymerizable functional groups; a compound having one or more homopolymerizable functional groups; or a compound having one homopolymerizable functional group which is also reactive with the epithio structure.

Examples of the compound having two or more functional groups reactive with the epithio structure include epoxy compounds, known episulfide compounds and anhydrides of polybasic carboxylic acids.

Examples of the epoxy compounds include phenol epoxy compounds which are condensation products of epihalohydrins with polyhydric phenols such as hydroquinone, catechol, resorcinol, bisphenol A, bisphenol F, bisphenol sulfone, bisphenol ether, bisphenol sulfide, halogenated bisphenol A and novolak resins; alcohol epoxy compounds which are condensation products of epihalohydrins with polyhydric alcohols such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerol, trimethylolpropane trimethacrylate, pentaerythritol, 1,3- or 1,4-cyclohexanediol, 1,3- or 1,4-cyclohexanedimethanol, hydrogenated bisphenol A, bisphenol A/ethylene oxide adducts and bisphenol A/propylene oxide adducts; glycidyl ester epoxy compounds which are condensation products of epihalohydrins with polybasic carboxylic acids such as adipic acid, sebacic acid, dodecandicarboxylic acid, dimer acid, phthalic acid, isophthalic acid, terephthalic acid, tetrahydrophthalic acid, methyltetrahydrophthalic acid, hexahydrophthalic acid, hexahydroisophthalic acid, hexahydroterephthalic acid, HET acid, nadic acid, maleic acid, succinic acid, fumaric acid, trimellitic acid, benzenetetracarboxylic acid, benzophenonetetracarboxylic acid, naphthalenedicarboxylic acid and diphenyldicarboxylic acid; amine epoxy compounds which are condensation products of epihalohydrins with primary amines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl)ether, 1,2-bis(3-aminopropoxy)ethane, 1,3-bis(3-aminopropoxy)-2,2'-dimethylpropane, 1,2-, 1,3- or 1,4-bisaminocyclohexane, 1,3- or 1,4-bisaminomethylcyclohexane, 1,3- or 1,4-bisaminoethylcyclohexane, 1,3- or 1,4-bisaminopropylcyclohexane, hydrogenated 4,4'-diaminodiphenylmethane, isophoronediamine, 1,4-bisaminopropylpiperadine, m- or p-phenylenediamine, 2,4- or 2,6-tolylenediamine, m- or p-xylylenediamine, 1,5- or 2,6-naphthalenediamine, 4,4'-diaminodiphenylmethane, 4,4'-diaminodiphenyl ether and 2,2-(4,4'-diaminodiphenyl)propane; amine epoxy compounds which are condensation products of epihalohydrins with secondary amines such as N,N'-dimethylethylene diamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- or 2,6-dimethylpiperadine, homopiperadine, 1,1-di(4-piperidyl)methane, 1,2-di(4-piperidyl)ethane, 1,3-di(4-piperidyl)prop ane and 1,4-di(4-piperidyl)butane; alicyclic epoxy compounds such as 3,4-epoxycyclohexyl-3,4-epoxycyclohexanecarboxylate, vinylcyclohexane dioxide, 2-(3,4-epoxycyclohexyl)-5,5-spiro-3,4-epoxycyclohexane-meta-dioxane and bis(3,4-epoxycyclohexyl)adipate; epoxy compounds produced by epoxidation of unsaturated compounds such as cyclopentadiene epoxide, epoxidized soy bean oil, epoxidized polybutadiene and vinylcyclohexene epoxide; and urethane epoxy compounds produced by the reaction between the polyhydric alcohols and phenols recited above with diisocyanates and glycidol.

Examples of the episulfide compound include compounds obtained by partially or entirely converting the epoxy groups in the above epoxy compounds into episulfide group.

Examples of the polybasic carboxylic acid anhydride include anhydrides of the acids described above as the compounds to be condensed with epihalohydrins.

Examples of the compound having one or more functional groups reactive with the epithio structure and one or more other homopolymerizable functional groups include epoxy compounds, episulfide compounds and carboxylic acid anhydrides each having an unsaturated group such as methacryl group, acryl group, allyl group, vinyl group and aromatic vinyl group.

Examples of the epoxy compounds having the unsaturated group include vinylphenyl glycidyl ether, vinylbenzyl glycidyl ether, glycidyl methacrylate, glycidyl acrylate and allyl glycidyl ether.

Examples of the compound having one or more homopolymerizable functional group include compounds having an unsaturated group such as methacryl group, acryl group, allyl group, vinyl group and aromatic vinyl group. Examples thereof include compounds having an ester structure derived from (meth)acrylic acid and a mono- or polyhydric alcohol, such as methyl acrylate, methyl methacrylate, ethyl acrylate, ethyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, polyethylene glycol diacrylate, polyethylene glycol dimethacrylate, 1,3-butylene glycol diacrylate, 1,3-butylene glycol dimethacrylate, 1,6-hexane diol diacrylate, 1,6-hexanediol dimethacrylate, neopentyl glycol diacrylate, neopentyl glycol dimethacrylate, polypropylene glycol diacrylate, polypropylene glycol dimethacrylate, 2,2-bis[4-(acryloxyethoxy)phenyl]propane, 2,2-bis[4-(methacryloxyethoxy)phenyl]propane, 2,2-bis [4-(acryloxy.diethoxy)phenyl]propane, 2,2-bis [4-(methacryloxy.diethoxy)phenyl]propane, 2,2-bis [4-(acryloxy.polyethoxy)phenyl]propane, 2,2-bis [4-(methacryloxy.polyethoxy)phenyl]propane, trimethylolpropane triacrylate, trimethylolpropane trimethacrylate, pentarythritol tetraacrylate, pentaerythritol tetramethacrylate, bis(2,2,2-trimethylolethyl)ether hexaacrylate and bis(2,2,2-trimethylolethyl)ether hexamethacrylate; allyl compounds such as allyl sulfide, diallyl phthalate and diethylene glycol bisallylcarbonate; vinyl compounds such as acrolein, acrylonitrile and vinyl sulfide; and aromatic vinyl compounds such as styrene, α-methylstyrene, methylvinylbenzene, ethylvinylbenzene, α-chlorostyrene, chlorovinylbenzene, vinylbenzyl chloride, p-divinylbenzene and m-divinylbenzene.

Examples of the compound having one homopolymerizable functional group which is also reactive with the epithio structure are compounds having one epoxy group or episulfide group. Specific examples of such compounds are monoepoxy compounds such as ethylene oxide, propylene oxide and glycidol; glycidyl esters of monocarboxylic acids such as acetic acid, propionic acid and benzoic acid; glycidyl ethers such as methyl glycidyl ether, ethyl glycidyl ether, propyl glycidyl ether and butyl glycidyl ether; monoepisulfides such as ethylene sulfide and propylene sulfide; and thioglycidyl esters having a structure derived from the above monocarboxylic acids and thioglycidol (1,2-epithio-3-hydroxypropane). Among these compounds, compounds having one episulfide group are preferable.

When the compound having one or more functional groups reactive with the epithio structure of Formula 2, or the compound having one or more functional groups reactive with the epithio structure and one or more other homopolymerizable functional groups is used, the polymerization for curing is preferably carried out in the presence of a curing catalyst that is described above.

When the composition of the present invention is cured by the polymerization with the compound having an unsaturated group, the polymerization is preferably conducted in the presence of a radical polymerization initiator as the polymerization accelerator. Any compound forming a radical by heating, ultraviolet light irradiation or electron beams irradiation, such as known heat polymerization catalysts and photopolymerization catalysts, can be used as the radical polymerization initiator. Examples of the heat polymerization catalysts are peroxides such as cumyl peroxyneodecanoate, diisopropyl peroxydicarbonate, diallyl peroxydicarbonate, di-n-propyl peroxydicarbonate, dimyristyl peroxydicarbonate, cumyl peroxyneohexanoate, tert-hexyl peroxyneodecanoate, tert-butyl peroxyneodecanoate, tert-hexyl peroxyneohexanoate, tert-butyl peroxyneohexanoate, 2,4-dichlorobenzoyl peroxide, benzoyl peroxide, dicumyl peroxide and di-tert-butyl peroxide; hydroperoxides such as cumene hydroperoxide and tert-butyl hydroperoxide; and azo compounds such as 2,2'-azobis(4-methoxy-2,4-dimethylvaleronitrile), 2,2'-azobis(2-cyclopropyipropionitrile), 2,2'-azobis(2,4-dimethylvaleronitrile), 2,2'-azobisisobutyronitrile, 2,2'-azobis(2-methylbutyronitrile), 1,1'-azobis(cyclohexane-1-carbonitrile), 1-[(1-cyano-1-methylethyl)azol]formamide, 2-phenylazo-4-methoxy-2,4-dimethylvaleronitrile, 2,2'-azobis(2-methylpropane) and 2,2'-azobis(2,4,4-trimethylpentane). Examples of the photopolymerization catalysts are benzophenone and benzoin benzoinmethyl ether. Among these compounds, peroxides, hydroperoxides and azo compounds are preferable and peroxides and azo compounds are more preferable. Most preferable examples include azo compounds such as 2,2'-azobis(4-methoxy-2,4-dimethylvaleronitrile), 2,2'-azobis(2-cyclopropylpropionitrile), 2,2'-azobis(2,4-dimethylvaleronitrile), 2,2'-azobisisobutyronitrile, 2,2'-azobis(2-methylbutyronitrile), 1,1'-azobis(cyclohexane-1-carbonitrile), 1-[(1-cyano-1-methylethyl)azo]formamide, 2-phenylazo-4-methoxy-2,4-dimethylvaleronitrile, 2,2'-azobis(2-methylpropane) and 2,2'-azobis(2,4,4-trimethylpentane). The above compounds may be used singly or in combination of two or more.

Although the amount of the radical polymerization initiator to be used varies depending on the components of the composition and the process for curing and is not strictly limited, the amount is preferably 0.01 to 5.0 parts by weight and more preferably 0.1 to 2.0 parts by weight based on 100 parts by weight of the episulfide compound.

The starting composition may contain, in addition to the above optional components, an oligomer of episulfide compound, the solvent or acid used in the episulfide compound synthesis, or the non-reacted compound or by-product in the episulfide compound synthesis in an amount not adversely affecting the object and effect of the present invention.

To improve the practical properties of the high refractive resin being produced by the method of the present invention, the composition may be added with known additives such as antioxidants, ultraviolet light absorbents, anti-yellowing agents, bluing agents and pigments. When the cured resin (optical material) is easy to separate from molds during polymerization, it is effective to use a known external and/or internal adhesion improver, thereby controlling and improving the adhesion between the cured material being formed and the mold. Examples of the internal adhesion improver include silane compounds such as 3-methacryloxypropyltrimethoxysilane, 3-glycidoxypropyltrimethoxysilane, N-(2-aminoethyl)-3-aminopropyltrimethoxysilane and 3-mercaptopropyltrimethoxysilane. The internal adhesion improver can be used in an amount of 0.0001 to 5 parts by weight per 100 parts by weight of the episulfide compound. On the other hand, when the cured resin is difficult to release from molds after the polymerization, it is effective to use a known external or internal mold releasing agent, thereby improving the releasability from the molds of the cured material being formed. Examples of the internal mold releasing agent include nonionic fluorine-containing surfactants, nonionic silicon-containing surfactants, quaternary alkylammonium salts, esters of phosphoric acid, acid esters of phosphoric acid, acid esters of phosphoric acid of oxyalkylene types, alkali metal salts of acid esters of phosphoric acid, alkali metal salts of oxyalkylene type acid ester of phosphoric acid, metal salts of higher fatty acids, esters of higher fatty acids, paraffin, wax, higher aliphatic amides, higher aliphatic alcohols, polysiloxanes and addition products of ethylene oxide and aliphatic amines. The internal mold releasing agent can be used in an amount of 0.0001 to 5 parts by weight, preferably 0.0005 to 3 parts by weight per 100 parts by weight of the episulfide compound.

In the present invention, the essential components (the episulfide compound and the polymerization regulator and/or the halogen-containing stabilizer) and the optional components (additives such as the compounds mentioned above, curing catalyst, radical polymerization initiator, adhesion improver, antioxidant, ultraviolet absorber and stabilizer) are mixed into a composition, which is then cast into a mold made of glass or metal, cured by polymerization under heating, and then released from the mold to obtain the high refractive resin (optical material). The essential components and the optional components may be all blended simultaneously in the same container, or may be blended by adding each component stepwise. Alternatively, a few of the components are separately blended and then blended together in the same container. The order of the blending of each essential component and each optional component is not particularly limited. The polymerization regulator and the halogen-containing stabilizer are preferably blended prior to the addition of the curing catalyst or simultaneously with the addition of the curing catalyst. When the polymerization regulator and the halogen-containing stabilizer are combinedly used, either one may be blended before the other as far as these are blended prior to the addition of the curing catalyst or simultaneously with the addition of the curing catalyst.

The mixing temperature and time are not critical as far as the components are sufficiently mixed. An excessively high temperature and an excessively long mixing time unfavorably make the casting operation difficult because undesirable reaction between the essential components and the optional components is induced to increase the viscosity. The mixing temperature is about −50 to 100° C., preferably −30 to 500° C., more preferably −5 to 30° C. The mixing time is one minute to five hours, preferably five minutes to two hours, more preferably 5 to 30 mm, and most preferably 5 to 15 min. The degasification under reduced pressure prior to the mixing, during the mixing or after the mixing of the essential components and the optional components is preferred to prevent the generation of bubbles during the subsequent casting step and curing step by polymerization. The degree of evacuation is about 0.1 to 700 mmHg, preferably 10 to 300 mmHg. To increase the quality of the optical material of the invention, it is preferred to remove impurities by filtering the starting materials before the casting into a mold through a filter having a pore size of about 0.05 to 5 μm.

The episulfide compound, the polymerization regulator and/or the halogen-containing stabilizer, and the optional components may be all or partly pre-reacted in the presence or absence of the catalyst with or without stirring, and then cast into a mold for curing. The pre-reaction is carried out at −100 to 160° C. for 0.1 to 100 h, preferably at −100 to 160° C. for 0.1 to 72 h, more preferably at −10 to 100° C. for 1 to 48 h, and most preferably at 0 to 60° C. for 1 to 48 h.

The curing time is 0.1 to 200 h, preferably 1 to 100 h, more preferably 1 to 48 h. The curing temperature is −10 to 160° C., preferably −10 to 140° C. The polymerization is carried out by keeping the starting mixture at a given polymerization temperature for a given period of time while raising the temperature at 0.1 to 100° C./h, lowering the temperature at 0.1 to 100° C./h or using a combination thereof. After curing, it is preferred to anneal the optical material at 50 to 150° C. for 10 mm to 5 h because the strain of the optical material can be removed. The optical material may be further subjected to surface treatment for improving dyeability, providing a hard coat or an impact resistant coat, and imparting non-reflection and non-fogging properties, etc.

The present invention will be described in more detail by reference to the following examples which should not be construed to limit the scope of the invention thereto.

The optical distortion, the striae, the separation from mold during polymerization, and the coloring in Examples 1 to 12 and Comparative Examples 1 to 8 were evaluated according to the following ratings.

Ratings for the Separation from Mold
  A: 95% or more yield (good)
  B: 90% or more yield and less than 95% yield (good)
  C: less than 90% yield (poor)

Ratings for the Coloring by Visual Observation
  A: colorless transparent (good)
  B: slightly yellowed (good)
  C: markedly yellowed (poor)

Ratings for the Optical Distortion
  The distortion was measured by a polariscope (PS-5 available from Riken Keiki Co., Ltd.)
  A: no distortion (good)
  B: slight distortion (good)
  C: appreciable distortion (poor)

Ratings for the Striae
  Measured by visual observation according to Schlieren method. A: no striae (good) B: slight striae (good) C: appreciable striae (poor)

EXAMPLE 1

A mixture of 4000 g of bis(β-epithiopropyl)sulfide, 20 g of N,N-diethylethanolamine (catalyst) and 32 g of mercaptomethyl thiirane (polymerization regulator) was cast into 100 pieces of—6D lens molds made of two glass plates. Then, the mixture was cured by polymerization in an oven by heating from 20 to 120° C. over 20 h. The evaluation results of the optical distortion, the striae, the coloring, and the separation form mold were shown in Table 1. The results were good in all the tested items.

EXAMPLE 2

A mixture of 4000 g of bis(β-epithiopropyl)sulfide, 20 g of N,N-diethylethanolamine (catalyst) and 0.02 g of mercaptomethyl thiirane (polymerization regulator) was tested in the same manner as in Example 1. The evaluation results were good in all the optical distortion, the striae, the coloring, and the separation form mold.

EXAMPLE 3

A mixture of 4000 g of bis(β-epithiopropyl)sulfide, 20 g of N,N-diethylethanolamine (catalyst) and 8 g of mercaptomethyl thiirane (polymerization regulator) was tested in the same manner as in Example 1. The evaluation results were good in all the optical distortion, the striae, the coloring, and the separation form mold.

EXAMPLE 4

A mixture of 4000 g of bis(β-epithiopropyl)sulfide, 20 g of N,N-diethylethanolamine (catalyst) and 16 g of methoxymethyl thiirane (polymerization regulator) was tested in the same manner as in Example 1. The evaluation results were good in all the optical distortion, the striae, the coloring, and the separation form mold.

EXAMPLE 5

A mixture of 4000 g of bis(β-epithiopropyl)sulfide, 20 g of N,N-diethylethanolamine (catalyst) and 0.4 g of chloromethyl thiirane (polymerization regulator) was tested in the same manner as in Example 1. The evaluation results were good in all the optical distortion, the striae, the coloring, and the separation form mold.

COMPARATIVE EXAMPLE 1

The procedure of Example 1 was repeated except for using no polymerization regulator. The evaluation results were poor in all the optical distortion, the striae, the coloring, and the separation form mold.

EXAMPLE 6

A mixture of 4000 g of bis(β-epithiopropyl)sulfide, 4 g of tetra-n-butyiphosphoniumbromide (catalyst) and 0.4 g of chloromethyl thiirane (polymerization regulator) was tested in the same manner as in Example 1. The evaluation results were good in all the optical distortion, the striae, the coloring, and the separation form mold.

COMPARATIVE EXAMPLE 2

The procedure of Example 5 was repeated except for using no polymerization regulator. The evaluation results were poor in all the optical distortion, the striae, the coloring, and the separation form mold.

EXAMPLE 7

A mixture of 4000 g of 1,2-bis(β-epithiopropylthio) ethane, 20 g of N,N-diethylethanolamine (catalyst) and 6 g of mercaptomethyl thiirane (polymerization regulator) was tested in the same manner as in Example 1. The evaluation results were good in all the optical distortion, the striae, the coloring, and the separation form mold.

COMPARATIVE EXAMPLE 3

The procedure of Example 6 was repeated except for using no polymerization regulator. The evaluation results were poor in all the optical distortion, the striae, the coloring, and the separation form mold.

EXAMPLE 8

A mixture of 4000 g of 1-(β-epithiopropylthio)-2-[2-β-epithiopropylthioethylthio]ethane, 20 g of N,N-diethylethanolamine (catalyst) and 4 g of methoxymethyl thiirane (polymerization regulator) was tested in the same manner as in Example 1. The evaluation results were good in all the optical distortion, the striae, the coloring, and the separation form mold.

COMPARATIVE EXAMPLE 4

The procedure of Example 7 was repeated except for using no polymerization regulator. The evaluation results were poor in all the optical distortion, the striae, the coloring, and the separation form mold.

EXAMPLE 9

A mixture of 4000 g of 2,5-bis(β-epithiopropylthiomethyl)-4,4dithiane, 30 g of N,N-diethylethanolamine (catalyst) and 0.8 g of chloromethyl thiirane (polymerization regulator) was tested in the same manner as in Example 1. The evaluation results were good in all the optical distortion, the striae, the coloring, and the separation form mold.

COMPARATIVE EXAMPLE 5

The procedure of Example 8 was repeated except for using no polymerization regulator. The evaluation results were poor in all the optical distortion, the striae, the coloring, and the separation form mold.

EXAMPLE 10

A mixture of 4000 g of 1,2,3-tris(β-epithiopropylthio) proPane, 15 g of N,N-dimethylcyclohexylamine (catalyst) and 6 g of mercaptomethyl thiirane (polymerization regulator) was tested in the same manner as in Example 1. The evaluation results were good in all the optical distortion, the striae, the coloring, and the separation form mold.

COMPARATIVE EXAMPLE 6

The procedure of Example 9 was repeated except for using no polymerization regulator. The evaluation results were poor in all the optical distortion, the striae, the coloring, and the separation form mold.

EXAMPLE 11

A mixture of 4000 g of 1,5-bis(β-epithiopropylthio)-2-(β-epithiopropylthiomethyl)-3-thiapentane, 15 g of N,N-dimethylcyclohexylamine (catalyst) and 4 g of methoxymethyl thiirane (polymerization regulator) was tested in the same manner as in Example 1. The evaluation results were good in all the optical distortion, the striae, the coloring, and the separation form mold.

COMPARATIVE EXAMPLE 7

The procedure of Example 10 was repeated except for using no polymerization regulator. The evaluation results were poor in all the optical distortion, the striae, the coloring, and the separation form mold.

EXAMPLE 12

A mixture of 4000 g of bis(β-epithiopropyl)disulfide, 13 g of N,N-dimethylcyclohexylamine (catalyst) and 2 g of chloromethyl thiirane (polymerization regulator) was tested in the same manner as in Example 1. The evaluation results were good in all the optical distortion, the striae, the coloring, and the separation form mold.

COMPARATIVE EXAMPLE 8

The procedure of Example 11 was repeated except for using no polymerization regulator. The evaluation results were poor in all the optical distortion, the striae, the coloring, and the separation form mold.

TABLE 1

| | Sulfide Compound | Polymerization catalyst | Polymerization regulator |
|---|---|---|---|
| Ex. 1 | A* | a* | mercaptomethyl thiirane |
| Ex. 2 | A* | a* | mercaptomethyl thiirane |
| Ex. 3 | A* | a* | mercaptomethyl thiirane |
| Ex. 4 | A* | a* | methoxymethyl thiirane |
| Ex. 5 | A* | a* | chloromethyl thiirane |
| Com. Ex. 1 | A* | a* | — |
| Ex. 6 | A* | b* | chloromethyl thiirane |
| Com. Ex. 2 | A* | b* | — |
| Ex. 7 | B* | a* | mercaptomethyl thiirane |
| Com. Ex. 3 | B* | a* | — |
| Ex. 8 | C* | a* | methoxymethyl thiirane |
| Com. Ex. 4 | C* | a* | — |
| Ex. 9 | D* | a* | chloromethyl thiirane |
| Com. Ex. 5 | D* | a* | — |
| Ex. 10 | E* | c* | mercaptomethyl thiirane |
| Com. Ex. 6 | E* | c* | — |
| Ex. 11 | F* | c* | methoxymethyl thiirane |
| Com. Ex. 7 | F* | c* | — |
| Ex. 12 | G* | c* | chloromethyl thiirane |
| Com. Ex. 8 | G* | c* | — |

| | Optical distortion | Striae | Separation form mold | Coloring |
|---|---|---|---|---|
| Ex. 1 | A | B | A | A |
| Ex. 2 | B | B | B | B |
| Ex. 3 | A | A | A | A |
| Ex. 4 | A | A | A | A |
| Ex. 5 | A | A | A | A |
| Com. Ex. 1 | C | C | C | C |
| Ex. 6 | A | A | A | A |
| Com. Ex. 2 | C | C | C | C |
| Ex. 7 | A | A | A | A |
| Com. Ex. 3 | C | C | C | C |
| Ex. 8 | A | A | A | A |
| Com. Ex. 4 | C | C | C | C |

TABLE 1-continued

| Ex. 9 | A | A | A | A |
|---|---|---|---|---|
| Com. Ex. 5 | C | C | C | C |
| Ex. 10 | A | A | A | A |
| Com. Ex. 6 | C | C | C | C |
| Ex. 11 | A | A | A | A |
| Com. Ex. 7 | C | C | C | C |
| Ex. 12 | A | A | A | A |
| Com. Ex. 8 | C | C | C | C |

A*: bis(β-epithiopropyl) sulfide
B*: 1,2-bis(β-epithiopropylthio)ethane
C*: 1-(β-epithiopropylthio)-2-[2-β-epithiopropylthioethylthio]ethane
D*: 2,5-bis(β-epithiopropylthiomethyl)-1,4-dithiane
E*: 1,2,3-tris(β-epithiopropylthio)propane
F*: 1,5-bis(β-epithiopropylthio)-2-(β-epithiopropylthiomethyl)-3-thiapentane
G*: bis(β-epithiopropyl) disulfide
a*: N,N-dimethylethanolamine
b*: tetra-n-butylphosphonium bromide
c*: N,N-dimethylcyclohexylamine EXAMPLES 13 to 28

Into 100 parts by weight of the compound or composition shown in Table 2, were added 0.1 part by weight of tetrabutyiphosphonium bromide (catalyst) and 500 ppm of the stabilizer shown in Table 2. The mixture was stirred to a homogeneous mixture, which was then kept at 40° C. to measure the viscosity by a Brookfield viscometer. The results are shown in Table 2.

TABLE 2

| Examples | Compound (weight ratio) | Halogen-containing stabilizer | Viscosity (cps) after 3 h | after 5 h |
|---|---|---|---|---|
| 13 | BES = 100 | Ph₃SbCl₂ | 20 | 25 |
| 14 | BES = 100 | Ph₃GeCl | 20 | 20 |
| 15 | BES = 100 | Bu₂SnCl₂ | 20 | 30 |
| 16 | BES = 100 | SnCl₄ | 20 | 35 |
| 17 | BESe = 100 | Ph₃SbCl₂ | 25 | 35 |
| 18 | BESe = 100 | Bu₂SnCl₂ | 25 | 45 |
| 19 | BED = 100 | Bu₃SnCl | 20 | 25 |
| 20 | BED = 100 | Ph₃GeCl | 20 | 20 |
| 21 | BDS = 100 | Me₂SiCl₂ | 25 | 35 |
| 22 | BDS = 100 | monochlorosuccinic acid | 25 | 65 |
| 23 | BEE = 100 | Et₂GaCl | 25 | 30 |
| 24 | BES/S = 90/10 | BuSnCl₃ | 30 | 40 |
| 25 | BSD/BMES = 95/5 | Ph₃GeCl | 25 | 35 |
| 26 | BES/DMMD/BIC = 80/14/6 | Ph₃SbCl₂ | 35 | 45 |
| 27 | BES/PETMA/NBDI = 60/27/13 | BuSnCl₃ | 40 | 55 |
| 28 | BES/S/PETMA/XDI = 75/3/14/8 | Bu₂SnCl₂ | 30 | 35 |

BES: bis(β-epithiopropyl) sulfide
BESe: bis(β-epithiopropyl) selenide
BED: bis(β-epithiopropyl) disulfide
BDS: bis(β-epidithiopropyl) sulfide
BEE: bis(β-epithioethyl) sulfide
BIC: 1,3-bis(isocyanatomethyl)cyclohexane
NBDI: 2,5-diisocyanatomethylnorbornene
XDI: m-xylylenediisocyanate
BMES: bis(2-mercaptoethyl) sulfide
DMMD: 2,5-dimercaptomethyl-1,4-dithiane
PETMA: pentaerythritol tetramercaptoacetate
S: sulfur COMPARATIVE EXAMPLES 9 to 18

Into 100 parts by weight of the compound or composition shown in Table 2, were added 0.1 part by weight of tetrabutyiphosphonium bromide (catalyst). The mixture was stirred to a homogeneous mixture, which was then kept at 40° C. in nitrogen atmosphere to measure the viscosity by a Brookfield viscometer. The results are shown in Table 3.

TABLE 3

| | Compound (weight ratio) | Halogen-containing stabilizer | Viscosity (cps) after 3 h | after 5 h |
|---|---|---|---|---|
| 9 | BES = 100 | none | 20 | 300 |
| 10 | BESe = 100 | none | 25 | 280 |
| 11 | BED = 100 | none | 20 | 250 |
| 12 | BDS = 100 | none | 25 | 230 |
| 13 | BEE = 100 | none | 25 | 450 |
| 14 | BES/S = 90/10 | none | 90 | solidified |
| 15 | BSD/BMES = 95/5 | none | 70 | 700 |
| 16 | BES/DMMD/BIC = 80/14/6 | none | solidified | — |
| 17 | BES/PETMA/NBDI = 60/27/13 | none | solidified | — |
| 18 | BES/S/PETMA/XDI = 75/3/14/8 | none | solidified | — |

BES: bis(β-epithiopropyl) sulfide
BESe: bis(β-epithiopropyl) selenide
BED: bis(β-epithiopropyl) desulfide
BDS: bis(β-epidithiopropyl) sulfide
BEE: bis(β-epithioethyl)sulfide
BIC: 1,3-bis(isocyanatomethyl)cyclohexane
NBDI: 2,5-diisocyanatomethylnorbornene
XDI: m-xylylenediisocyanate
BMES: bis(2-mercaptoethyl) sulfide
DMMD: 2,5-dimercaptomethyl-1,4-dithiane
PETMA: pentaerythritol tetramercaptoacetate
S: sulfur

INDUSTRIAL APPLICABILITY

According to the present invention, the polymerization of the episulfide compound can be suitably regulated by using the polymerization regulator represented by Formula 1. In addition, the increase in the viscosity of the starting composition during the storage can be prevented by adding the halogen-containing stabilizer. The increase in the viscosity after adding the polymerization catalyst and before the initiation of the curing reaction can be also prevented. Thus, the invention improves the workability during the molding step and enables the easy production of the optical resin material with a sufficiently high refractive index and a good Abbe's number.

The invention claimed is:

1. A composition for resin comprising an episulfide compound having, in one molecule, at least one epithio structure represented by the following Formula 2:

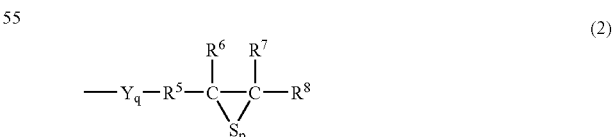

(2)

wherein $R^5$ is C1–C10 hydrocarbylene or single bond, $R^6$, $R^7$ and $R^8$ are each independently C1–C10 hydrocarbyl or hydrogen, Y is O, S, Se or Te, p is an integer from 1 to 5, and q is an integer from 0 to 5, and at least one halide of a 13–16 group element of the long periodic table as a stabilizer for the episulfide compound, wherein the halide is represented by the following Formula 5:

wherein $R^{17}$ is C1–C8 alkyl, C1–C4 alkoxyl or phenyl; M is silicon, germanium, tin or antimony; $X^2$ is halogen, halogenated alkyl, halogenated alkenyl, halogenated alkoxyl, or halogenated aryl; s is an integer including zero; t is an integer of 1 or more, with s+t being equal to the valency of M; and when s is an integer of two or more, a plurality of $R^{17}$ groups may be the same or different.

2. The composition for resin according to claim 1, wherein Y is S or Se, $R^5$ is a single bond or methylene, p is 1, and q is 1 or 2.

3. The composition for resin according to claim 2, which contains 0.001 to 10 parts by weight of the halide based on 100 parts by weight of the episulfide compound.

4. The composition for resin according to claim 1, which contains 0.001 to 10 parts by weight of the halide based on 100 parts by weight of the episulfide compound.

5. A method for producing a resin for optical material, which comprises a step of polymerizing an episulfide compound having, in one molecule, at least one epithio structure represented by the following Formula 2:

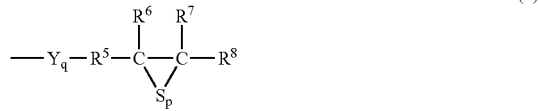

wherein $R^5$ is C1–C10 hydrocarbylene or single bond, $R^6$, $R^7$ and $R^8$ are each independently C1–C10 hydrocarbyl or hydrogen, Y is O, S, Se or Te, p is an integer from 1 to 5, and q is an integer from 0 to 5, in the presence of a halide of a 13–16 group element of the long periodic table as a stabilizer of the episulfide compound, wherein the halide is represented by the following Formulation 5:

wherein $R^{17}$ is C1–C8 alkyl, C1–C4 alkoxyl or phenyl; M is silicon, germanium, tin or antimony; $X^2$ is halogen, halogenated alkyl, halogenated alkenyl, halogenated alkoxyl, or halogenated aryl; s is an integer including zero; t is an integer of 1 or more, with s+t being equal to the valency of M; and when s is an integer of two or more, a plurality of $R^{17}$ groups may be the same or different.

6. The method according to claim 5, wherein 0.0001 to 10 part by weight of the halide is used based on 100 parts by weight of the episulfide compound.

7. The method according to claim 5, wherein the polymerization is carried out in the presence of a curing catalyst.

8. The method according to claim 7, wherein the halide is added before the addition of the curing catalyst or is added simultaneously with the addition of the curing catalyst.

9. The method according to claim 5, wherein the episulfide compound has at least two epithio structures represented by the following Formula 3:

wherein $R^6$ to $R^8$ and p are as defined above.

10. The method according to claim 9, wherein the episulfide compound is represented by the following Formula 4:

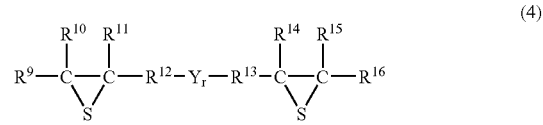

wherein $R^{12}$ and $R^{13}$ are each C1–C10 hydrocarbylene or single bond, $R^9$ to $R^{11}$ and $R^{14}$ to $R^{16}$ are each C1–C10 hydrocarbyl or hydrogen, Y is O, S, Se or Te, and r is an integer from 1 to 5.

11. The method according to claim 10, wherein the polymerization is carried out at −10 to 160° C. for 0.1 to 200 h.

12. The method according to claim 6, wherein the polymerization is carried out in the presence of a curing catalyst.

13. The method according to claim 7, wherein the episulfide compound has at least two epithio structures represented by the following Formula 3:

wherein $R^6$ to $R^8$ and p are as defined above.

14. The method according to claim 7, wherein the episulfide compound is represented by the following Formula 4:

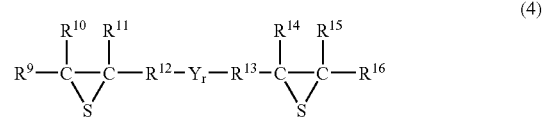

wherein $R^{12}$ and $R^{13}$ are each C1–C10 hydrocarbylene or single bond, $R^9$ to $R^{11}$ and $R^{14}$ to $R^{16}$ are each C1–C10 hydrocarbyl or hydrogen, Y is O, S, Se or Te, and r is an integer from 1 to 5.

15. The method according to claim 5, wherein the episulfide compound is represented by the following Formula 4:

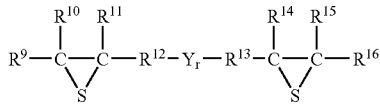 (4)

wherein $R^{12}$ and $R^{13}$ are each C1–C10 hydrocarbylene or single bond, $R^9$ to $R^{11}$ and $R^{14}$ to $R^{16}$ are each C1–C10 hydrocarbyl or hydrogen, Y is O, S, Se or Te, and r is an integer from 1 to 5.

16. The method according to claim 9, wherein the polymerization is carried out at −10 to 160° C. for 0.1 to 200 h.

17. The method according to claim 7, wherein the polymerization is carried out at −10 to 160° C. for 0.1 to 200 h.

18. The method according to claim 5, wherein the polymerization is carried out at −10 to 160° C. for 0.1 to 200 h.

19. A method for producing a resin for optical material, which comprises a step of polymerizing an episulfide compound having, in one molecule, at least one epithio structure represented by the following Formula 2:

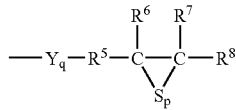 (2)

wherein $R^5$ is C1–C10 hydrocarbylene or single bond, $R^6$, $R^7$ and $R^8$ are each independently C1–C10 hydrocarbyl or hydrogen, Y is O, S, Se or Te, p is an integer from 1 to 5, and q is an integer from 0 to 5, in the presence of a halide of a 13–16 group element of the long periodic table, wherein the halide is represented by the following Formula 5:

$$R^{17}{}_s MX^2{}_t \qquad (5)$$

wherein $R^{17}$ is C1–C8 alkyl, C1–C4 alkoxyl or phenyl; M is silicon, germanium, tin or antimony; $X^2$ is halogen, halogenated alkyl, halogenated alkenyl, halogenated alkoxyl, or halogenated aryl; s is an integer including zero; t is an integer of 1 or more, with s+t being equal to the valency of M; and when s is an integer of two or more, a plurality of $R^{17}$ groups may be the same or different.

* * * * *